United States Patent
Barrow et al.

(10) Patent No.: US 9,266,881 B2
(45) Date of Patent: Feb. 23, 2016

(54) TRIAZOLOPYRIDINONE PDE10 INHIBITORS

(71) Applicant: Merck Sharp & Dohme Corp., Rahway, NJ (US)

(72) Inventors: James C. Barrow, Arnold, MD (US); Christopher D. Cox, Harleysville, PA (US); Mark B. Nolt, Lansdale, PA (US); William D. Shipe, Chalfont, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/357,690

(22) PCT Filed: Nov. 9, 2012

(86) PCT No.: PCT/US2012/064281
§ 371 (c)(1),
(2) Date: May 12, 2014

(87) PCT Pub. No.: WO2013/074390
PCT Pub. Date: May 23, 2013

(65) Prior Publication Data
US 2014/0343053 A1    Nov. 20, 2014

Related U.S. Application Data

(60) Provisional application No. 61/559,375, filed on Nov. 14, 2011.

(51) Int. Cl.
*C07D 471/04* (2006.01)
*C07D 401/14* (2006.01)
*C07D 413/14* (2006.01)
*C07D 401/06* (2006.01)
*C07D 403/06* (2006.01)
*C07D 417/14* (2006.01)

(52) U.S. Cl.
CPC ............ *C07D 471/04* (2013.01); *C07D 401/06* (2013.01); *C07D 401/14* (2013.01); *C07D 403/06* (2013.01); *C07D 413/14* (2013.01); *C07D 417/14* (2013.01)

(58) Field of Classification Search
CPC .................................................... C07D 471/04
See application file for complete search history.

(56) References Cited

U.S. PATENT DOCUMENTS

| | | |
|---|---|---|
| 3,381,009 A | 4/1968 | Silvestrini et al. |
| 2006/0009465 A1 | 1/2006 | Edgar et al. |
| 2007/0004772 A1 | 1/2007 | Sun et al. |
| 2007/0208029 A1 | 9/2007 | Barlow et al. |
| 2009/0143361 A1 | 6/2009 | Malamas et al. |

FOREIGN PATENT DOCUMENTS

| | | | |
|---|---|---|---|
| EP | 401707 A1 * | 12/1990 | ............ A61K 31/41 |
| WO | WO2006138695 | 12/2006 | |
| WO | WO2010117926 | 10/2010 | |
| WO | WO 2012003392 A1 * | 1/2012 | |

OTHER PUBLICATIONS

Becker et al., Phosphodiesterase Inhibitors—Are They Potential Neuroleptic Drugs?, Behavioural Brain research, 2008, pp. 155-160, 186.
Fujishige et al., Cloning and Characterization of a Novel Human Phosphodiesterase That Hydrolyzes Both cAMPand cGMP (PDE10A), J. of Biological Chemistry, Jun. 25, 1999, pp. 18438-18445, 274.
Huang et al., A Fluroescence Polarization Assay for Cyclic Nucleotide Phosphodiesterases, J. of Biomolecular Screening, 2002, pp. 215-222, 7.
Kehler, The Potential Therapeutic Use of Phosphodiesterase 10 Inhibitors, Expert Opinion, 2007, pp. 147-158, 17.
Lieberman et al., Effectiveness of Antipsychotic Drugs in Patients with Chronic Schizophrenia, New England J. of Medicine, Sep. 22, 2005, pp. 1209-1223, 353, US.
Loughney et al., Isolation and Characterization of PDE10A, a Novel Human 3', 5'-Cyclic Nucleotide Phosphodiesterase, Gene, 1999, pp. 109-117, 234.
Schmidt et al., Pre-clincal Characterization of Selective PHosphodiesterase 10A Inhibitors: A New Therapeutic Approach to the Treatment of Schizophrenia, J. of Pharmacology and Experimental Thereapeutics, 2008, pp. 690-690, 325.
Siuciak et al., Inhibiton of the Striatum-Enriched Phosphodiesterease PDE10A: A novel Approach to the Treament of Psychosis, Neuropharmacology, 2006, pp. 386-396, 51.
Soderling et al., Isolation and Characterization of a Dual-Substrate Phosphodiesterase Gene Family: PDE10A, Proc. Natl. Acad. Sci. USA, Jun. 1999, pp. 7071-7076, 96.
Threlfell et al., Inhibition of Phosphodiesterase 10A Increases the Responsiveness of Striatal Projection Neurons to the Cortical Stimulation, J. of Pharmacology and Experimental Therapeutics, J. of Pharmacology and Experimental Therapeutics, 2009, pp. 785-795, 328.
Database Registry Chemical Abstracts Service, Columbus, Ohio, US; Database Accession No. 1252151-66-8, XP002739437.
Database Registry Chemical Abstracts Service, Columbus, Ohio, US; Database Accession No. 1311711406, XP002739438.
Database Registry Chemical Abstracts Service; Dec. 28, 2008, Database Accession No. 1090617-34-7, XP002739436.

* cited by examiner

*Primary Examiner* — David K O Dell
(74) *Attorney, Agent, or Firm* — Sylvia A. Ayler; John C. Todaro

(57) ABSTRACT

The present invention is directed to triazolopyridinone compounds which are useful as therapeutic agents for the treatment of central nervous system disorders associated with phosphodiesterase 10 (PDE10). The present invention also relates to the use of such compounds for treating neurological and psychiatric disorders, such as schizophrenia, psychosis or Huntington's disease, and those associated with striatal hypofunction or basal ganglia dysfunction.

9 Claims, No Drawings

TRIAZOLOPYRIDINONE PDE10 INHIBITORS

CROSS REFERENCE TO RELATED APPLICATIONS

This application is the National Stage of International Application No. PCT/US2012/064281 filed on Nov. 9, 2012, which claims the benefit under 35 U.S.C. 119(e) of U.S. Provisional Application No. 61/559,375, filed Nov. 14, 2011.

FIELD OF THE INVENTION

The invention relates generally to compounds which act as inhibitors of the phosphodiesterase (PDE) 10 enzyme, compositions and therapeutic uses thereof.

BACKGROUND OF THE INVENTION

Schizophrenia is a debilitating disorder affecting the psychic and motor functions of the brain. It is typically diagnosed in individuals in their early to mid-twenties and symptoms include hallucinations and delusions or at the other extreme, anhedonia or social withdrawal. Across the spectrum, the symptoms are indicative of cognitive impairment and functional disabilities. Notwithstanding improvements in antipsychotic treatments, current therapies, including typical (haloperidol) and atypical (clozapine or olanzapine) antipsychotics, have been less than acceptable and result in an extremely high rate of noncompliance or discontinuation of medication. Dissatisfaction with therapy is attributed to lack of efficacy or intolerable and unacceptable side affects. The side effects have been associated with significant metabolic, extrapyramidal, prolactic and cardiac adverse events. See Lieberman et al., *N. Engl. J. Med.* (2005) 353:1209-1223.

While multiple pathways are believed to be involved with the pathogenesis of schizophrenia leading to psychosis and cognition deficits, much attention has focused on the role of glutamate/NMDA dysfunction associated with cyclic guanosine monophosphate (cGMP) levels and the dopaminergic D2 receptor associated with cyclic adenosine monophosphate (cAMP). These ubiquitous second messengers are responsible for altering the function of many intracellular proteins. Cyclic AMP is thought to regulate the activity of cAMP-dependent protein kinase (PKA), which in turns phosphorylates and regulates many types of proteins including ion channels, enzymes and transcription factors. Similarly, cGMP is also responsible for downstream regulation of kinases and ion channels.

One pathway for affecting the levels of cyclic nucleotides, such as cAMP and cGMP, is to alter or regulate the enzymes that degrade these enzymes, known as 3',5'-cyclic nucleotide specific phosphodiesterases (PDEs). The PDE superfamily includes twenty one genes that encode for eleven families of PDEs. These families are further subdivided based on catalytic domain homology and substrate specificity and include the 1) cAMP specific, PDE4A-D, 7A and 7B, and 8A and 8B, 2) cGMP specific, PDE 5A, 6A-C, and 9A, and 3) those that are dual substrate, PDE 1A-C, 2A, 3A and 3B, 10A, and 11A. The homology between the families, ranging from 20% to 45% suggests that it may be possible to develop selective inhibitors for each of these subtypes.

The identification of PDE10 was reported by three groups independently and was distinguished from other PDEs on the basis of its amino acid sequence, functional properties, and tissue distribution (Fujishige et al., *J. Biol. Chem.* (1999) 274:18438-18445; Loughney et al., *Gene* (1999) 234: 109-117; Soderling et al., *PNAS, USA* (1999) 96: 7071-7076). The PDE10 subtype at present consists of a sole member, PDE10A, having alternative splice variants at both the N-terminus (three variants) and C-terminus (two variants), but that does not affect the GAF domain in the N-terminus or the catalytic site in C-terminus. The N-terminus splice variants, PDE10A1 and PDE10A2, differ in that the A2 variant has a PKA phosphorylation site that upon activation, i.e. PKA phosphorylation in response to elevated cAMP levels, results in intracellular changes to the localization of the enzyme. PDE10A is unique relative to other PDE families also having the conserved GAF domain in that its ligand is cAMP, while for the other GAF-domain PDEs the ligand is cGMP (Kehler et al., *Expert Opin. Ther. Patents* (2007) 17(2): 147-158). PDE10A has limited but high expression in the brain and testes. The high expression in the brain and, in particular, the neurons of the striatum, unique to PDE10, suggests that inhibitors thereto may be well suited from treating neurological and psychiatric disorders and conditions.

Inhibition of PDE 10 is believed to be useful in the treatment of schizophrenia and a wide variety of conditions or disorders that would benefit from increasing levels of cAMP and/or cGMP within neurons, including a variety neurological, psychotic, anxiety and/or movement disorders. Accordingly, agents that inhibit PDE10 and especially PDE10A would be desirable as therapeutics for neurological and psychiatric disorders.

SUMMARY OF THE INVENTION

The present invention is directed to triazolopyridinone compounds which are useful as therapeutic agents for the treatment of central nervous system disorders associated with phosphodiesterase 10 (PDE10). The present invention also relates to the use of such compounds for treating neurological and psychiatric disorders, such as schizophrenia, psychosis or Huntington's disease, and those associated with striatal hypofunction or basal ganglia dysfunction.

DETAILED DESCRIPTION OF THE INVENTION

The present invention is directed to compounds of the formula I:

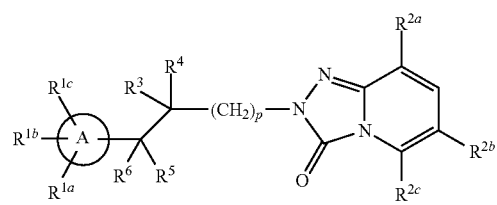

wherein:
A is heterocyclyl;
$R^{1a}$, $R^{1b}$ and $R^{1c}$ may be absent if the valency of A does not permit such substitution and are independently selected from the group consisting of:
(1) hydrogen,
(2) halogen,
(3) hydroxyl,
(4) —(C=O)$_m$—O$_n$—C$_{1-6}$alkyl, where m is 0 or 1, n is 0 or 1 (wherein if m is 0 or n is 0, a bond is present) and where the alkyl is unsubstituted or substituted with one or more substituents selected from $R^{13}$, (5) —(C=O)$_m$—O$_n$—C$_{3-6}$cycloalkyl, where the cycloalkyl is unsubstituted or substituted with one or more substituents selected from R$^{13}$,
(6) —(C=O)$_m$—C$_{2-4}$alkenyl, where the alkenyl is unsubstituted or substituted with one or more substituents selected from R$^{13}$,
(7) —(C=O)$_m$—C$_{2-4}$alkynyl, where the alkynyl is unsubstituted or substituted with one or more substituents selected from R$^{13}$,
(8) —(C=O)$_m$—O$_n$-phenyl or —(C=O)$_m$—O$_n$-naphthyl, where the phenyl or naphthyl is unsubstituted or substituted with one or more substituents selected from R$^{13}$,
(9) —(C=O)$_m$—O$_n$-heteroaryl, where the heteraryl is unsubstituted or substituted with one or more substituents selected from R$^{13}$,
(10) —(C=O)$_m$—NR$^{10}$R$^{11}$, wherein R$^{10}$ and R$^{11}$ are independently selected from the group consisting of:
  (a) hydrogen,
  (b) C$_{1-6}$alkyl, which is unsubstituted or substituted with R$^{14}$,
  (c) C$_{3-6}$alkenyl, which is unsubstituted or substituted with R$^{14}$,
  (d) C$_{3-6}$alkynyl, which is unsubstituted or substituted with R$^{14}$,
  (e) C$_{3-6}$cycloalkyl which is unsubstituted or substituted with R$^{14}$,
  (f) phenyl, which is unsubstituted or substituted with R$^{14}$, and
  (g) heteroaryl, which is unsubstituted or substituted with R$^{14}$,
(11) —S(O)$_2$—NR$^{10}$R$^{11}$,
(12) —S(O)$_q$—R$^{12}$, where q is 0, 1 or 2 and where R$^{12}$ is selected from the definitions of R$^{10}$ and R$^{11}$,
(13) —CO$_2$H,
(14) —CN, and
(15) —NO$_2$;

R$^{2a}$, R$^{2b}$ and R$^{2c}$ are independently selected from the group consisting of:
(1) hydrogen,
(2) halogen,
(3) hydroxyl,
(4) —(C=O)$_m$—O$_n$—C$_{1-6}$alkyl, where the alkyl is unsubstituted or substituted with one or more substituents selected from R$^{13}$,
(5) —(C=O)$_m$—O$_n$—C$_{3-6}$cycloalkyl, where the cycloalkyl is unsubstituted or substituted with one or more substituents selected from R$^{13}$,
(6) —(C=O)$_m$—C$_{2-4}$alkenyl, where the alkenyl is unsubstituted or substituted with one or more substituents selected from R$^{13}$,
(7) —(C=O)$_m$—C$_{2-4}$alkynyl, where the alkynyl is unsubstituted or substituted with one or more substituents selected from R$^{13}$,
(8) —(C=O)$_m$—O$_n$-phenyl or —(C=O)$_m$—O$_n$-naphthyl, where the phenyl or naphthyl is unsubstituted or substituted with one or more substituents selected from R$^{13}$,
(9) —(C=O)$_m$—O$_n$-heterocyclyl, where the heterocyclyl is unsubstituted or substituted with one or more substituents selected from R$^{13}$,
(10) —(C=O)$_m$—NR$^{10}$R$^{11}$,
(11) —S(O)$_2$—NR$^{10}$R$^{11}$,
(12) —S(O)$_q$—R$^{12}$,
(13) —CO$_2$H,
(14) —CN, and
(15) —NO$_2$;

R$^3$, R$^4$, R$^5$ and R$^6$ are independently selected from the group consisting of:
(1) hydrogen,
(2) halogen, and
(3) —C$_{1-6}$alkyl,
or R$^3$ and R$^5$ are joined together to form a cyclopropyl ring;

R$^{13}$ is selected from the group consisting of:
(1) halogen,
(2) hydroxyl,
(3) —(C=O)$_m$—O$_n$—C$_{1-6}$alkyl, where the alkyl is unsubstituted or substituted with one or more substituents selected from R$^{14}$,
(4) —O$_n$—(C$_{1-3}$)perfluoroalkyl,
(5) —(C=O)$_m$—O$_n$—C$_{3-6}$cycloalkyl, where the cycloalkyl is unsubstituted or substituted with one or more substituents selected from R$^{14}$,
(6) —(C=O)$_m$—C$_{2-4}$alkenyl, where the alkenyl is unsubstituted or substituted with one or more substituents selected from R$^{14}$,
(7) —(C=O)$_m$—C$_{2-4}$alkynyl, where the alkynyl is unsubstituted or substituted with one or more substituents selected from R$^{14}$,
(8) —(C=O)$_m$—O$_n$-phenyl or —(C=O)$_m$—O$_n$-naphthyl, where the phenyl or naphthyl is unsubstituted or substituted with one or more substituents selected from R$^{14}$,
(9) —(C=O)$_m$—O$_n$-heteroaryl, where the heteroaryl is unsubstituted or substituted with one or more substituents selected from R$^{14}$,
(10) —(C=O)$_m$—NR$^{10}$R$^{11}$,
(11) —S(O)$_2$—NR$^{10}$R$^{11}$,
(12) —S(O)$_q$—R$^{12}$,
(13) —CO$_2$H,
(14) —CN, and
(15) —NO$_2$;

R$^{14}$ is selected from the group consisting of:
(1) hydroxyl,
(2) halogen,
(3) C$_{1-6}$alkyl,
(4) —C$_{3-6}$cycloalkyl,
(5) —O—C$_{1-6}$alkyl,
(6) —O(C=O)—C$_{1-6}$alkyl,
(7) —NH—C$_{1-6}$alkyl,
(8) phenyl,
(9) heteroaryl,
(10) —CO$_2$H, and
(11) —CN;

p is 0 or 1, wherein when p is 0 a bond is present;
or a pharmaceutically acceptable salt thereof.

An embodiment of the present invention includes compounds of the formula Ia:

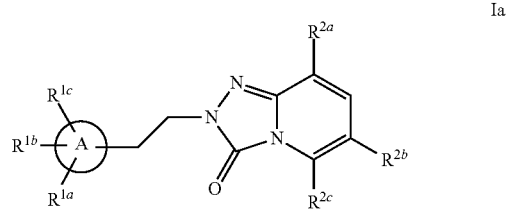

wherein A, R$^{1a}$, R$^{1b}$, R$^{1c}$, R$^{2a}$, R$^{2b}$, and R$^{2c}$ are defined herein; or a pharmaceutically acceptable salt thereof.

An embodiment of the present invention includes compounds of the formula Ib:

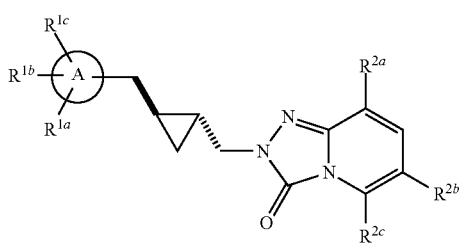

wherein A, $R^{1a}$, $R^{1b}$, $R^{1c}$, $R^{2a}$, $R^{2b}$, and $R^{2c}$ are defined herein; or a pharmaceutically acceptable salt thereof.

An embodiment of the present invention includes compounds of the formula Ic:

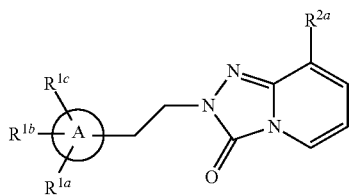

wherein A, $R^{1a}$, $R^{1b}$, $R^{1c}$ and $R^{2a}$ are defined herein; or a pharmaceutically acceptable salt thereof.

An embodiment of the present invention includes compounds of the formula Id:

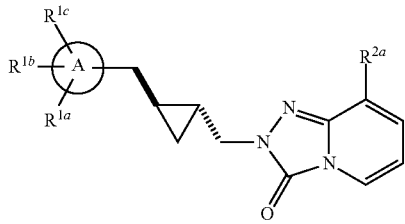

wherein A, $R^{1a}$, $R^{1b}$, $R^{1c}$ and $R^{2a}$ are defined herein; or a pharmaceutically acceptable salt thereof.

An embodiment of the present invention includes compounds of the formula Ie:

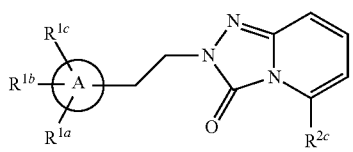

wherein A, $R^{1a}$, $R^{1b}$, $R^{1c}$ and $R^{2c}$ are defined herein; or a pharmaceutically acceptable salt thereof.

An embodiment of the present invention includes compounds of the formula If:

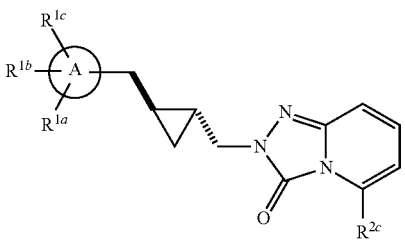

wherein A, $R^{1a}$, $R^{1b}$, $R^{1c}$ and $R^{2c}$ are defined herein; or a pharmaceutically acceptable salt thereof.

An embodiment of the present invention includes compounds wherein A is selected from the group consisting of:
(1) benzimidazolyl,
(2) imidazopyridinyl,
(3) naphthyridinyl,
(4) pyridopyrimidinone,
(5) quinazolinone,
(6) quinolinyl,
(7) quinoxalinyl, and
(8) tetrahydroquinolinyl.

An embodiment of the present invention includes compounds wherein A is selected from the group consisting of:
(1) benzimidazol-2-yl,
(2) imidazo[1,2-a]pyridin-2-yl,
(3) 1,5-naphthyridin-2-yl,
(4) pyrido[2,3-d]pyrimidin-4(3H)-one,
(5) quinazolin-4(3H)-one,
(6) quinoxalin-2-yl,
(7) quinolin-2-yl, and
(8) 5,6,7,8-tetrahydroquinolin-2-yl.

An embodiment of the present invention includes compounds wherein A is quinazolin-4(3H)-one. An embodiment of the present invention includes compounds wherein A is quinolin-2-yl. An embodiment of the present invention includes compounds wherein A is 1,5-naphthyridin-2-yl. An embodiment of the present invention includes compounds wherein A is 5,6,7,8-tetrahydroquinolin-2-yl. An embodiment of the present invention includes compounds wherein A is benzimidazol-2-yl. An embodiment of the present invention includes compounds wherein A is thiazol-4-yl.

An embodiment of the present invention includes compounds wherein $R^{1a}$, $R^{1b}$ and $R^{1c}$ are independently selected from the group consisting of:
(1) hydrogen,
(2) halogen,
(3) hydroxyl,
(4) $C_{1-6}$alkyl, which is unsubstituted or substituted with $C_{3-6}$cycloalkyl, halogen, hydroxyl, phenyl or naphthyl,
(5) —O—$C_{1-6}$alkyl, which is unsubstituted or substituted with halogen, hydroxyl or phenyl,
(6) $C_{3-6}$cycloalkyl, which is unsubstituted or substituted with $C_{1-6}$alkyl, halogen, hydroxyl, or phenyl,
(7) heteroaryl, wherein heteroaryl is selected from pyrrolyl, imidazolyl, indolyl, pyridyl, pyrazolyl, and pyrimidinyl, which is unsubstituted or substituted with halogen, hydroxyl, $C_{1-6}$alkyl, —O—$C_{1-6}$alkyl or —NO$_2$, and
(8) phenyl, which is unsubstituted or substituted with halogen, hydroxyl, $C_{1-6}$alkyl, —O—$C_{1-6}$alkyl or —NO$_2$.

An embodiment of the present invention includes compounds wherein $R^{1b}$ is hydrogen, $R^{1c}$ is hydrogen and $R^{1a}$ is independently selected from the group consisting of:

(1) hydrogen,
(2) chloro,
(3) fluoro,
(4) bromo,
(5) methyl,
(6) methoxy,
(7) (methyl)cyclopropyl-,
(8) cyclopropyl,
(9) (methoxy)phenyl-, and
(10) (methyl)phenyl-.

An embodiment of the present invention includes compounds wherein $R^{2a}$, $R^{2b}$ and $R^{2c}$ are independently selected from the group consisting of
(1) hydrogen,
(2) halogen,
(3) hydroxyl,
(4) $C_{1-6}$alkyl, which is unsubstituted or substituted with halogen, hydroxyl or phenyl or naphthyl,
(5) —O—$C_{1-6}$alkyl, which is unsubstituted or substituted with halogen, hydroxyl or phenyl,
(6) heterocyclyl, wherein heterocyclyl is selected from imidazolyl, isothiazolyl, oxazolyl, morpholinyl, pyrazolyl, pyridyl, tetrazolyl, pyrazinyl, and thiazolyl, which is unsubstituted or substituted with halogen, hydroxyl, $C_{1-6}$alkyl, —O—$C_{1-6}$alkyl or —NO$_2$, and
(7) phenyl, which is unsubstituted or substituted with halogen, hydroxyl, $C_{1-6}$alkyl, —O—$C_{1-6}$alkyl or —NO$_2$.

An embodiment of the present invention includes compounds wherein $R^{2b}$ is hydrogen, and $R^{2a}$ and $R^{2c}$ are independently selected from the group consisting of:
(1) hydrogen,
(2) chloro,
(3) fluoro,
(4) bromo,
(5) methyl,
(6) isopropoxy,
(7) methoxy,
(8) t-butoxy,
(9) imidazolyl,
(10) isothiazolyl,
(11) oxazolyl,
(12) morpholinyl,
(13) pyrazolyl,
(14) pyridyl,
(15) tetrazolyl, and
(16) thiazolyl.

An embodiment of the present invention includes compounds wherein $R^{2b}$ is hydrogen, $R^{2c}$ is hydrogen and $R^{2a}$ is selected from the group consisting of:
(1) hydrogen,
(2) chloro,
(3) fluoro,
(4) bromo,
(5) methyl,
(6) isopropoxy,
(7) methoxy,
(8) t-butoxy,
(9) imidazolyl,
(10) isothiazolyl,
(11) oxazolyl,
(12) morpholinyl,
(13) pyrazolyl,
(14) pyridyl,
(15) tetrazolyl, and
(16) thiazolyl.

An embodiment of the present invention includes compounds wherein $R^{2b}$ is hydrogen, $R^{2c}$ is hydrogen and $R^{2a}$ is selected from the group consisting of:
(1) chloro,
(2) methyl,
(3) isopropoxy,
(4) oxazolyl,
(5) pyrazolyl,
(6) pyridyl, and
(7) thiazolyl.

An embodiment of the present invention includes compounds wherein $R^{2b}$ is hydrogen, $R^{2a}$ is hydrogen and $R^{2c}$ is selected from the group consisting of:
(1) hydrogen,
(2) chloro,
(3) fluoro,
(4) bromo,
(5) methyl,
(6) isopropoxy,
(7) methoxy,
(8) t-butoxy,
(9) imidazolyl,
(10) isothiazolyl,
(11) oxazolyl,
(12) morpholinyl,
(13) pyrazolyl,
(14) pyridyl,
(15) tetrazolyl, and
(16) thiazolyl.

An embodiment of the present invention includes compounds wherein $R^{2b}$ is hydrogen, $R^{2a}$ is hydrogen and $R^{2c}$ is selected from the group consisting of:
(1) chloro,
(2) methyl,
(3) isopropoxy,
(4) oxazolyl,
(5) pyrazolyl,
(6) pyridyl, and
(7) thiazolyl.

An embodiment of the present invention includes compounds wherein p is 0.

An embodiment of the present invention includes compounds wherein p is 1 and $R^3$ and $R^5$ are joined together to form a cyclopropyl ring.

An embodiment of the present invention includes compounds wherein $R^3$ is hydrogen, $R^4$ is hydrogen, $R^5$ is hydrogen, and $R^6$ is hydrogen.

Specific embodiments of the present invention include a compound which is selected from the group consisting of the subject compounds of the Examples herein and pharmaceutically acceptable salts thereof and individual enantiomers and diastereomers thereof.

As appreciated by those of skill in the art, halogen or halo as used herein are intended to include fluorine, chlorine, bromine and iodine. Similarly, "alkyl", as well as other groups having the prefix "alk", such as alkoxy, alkanoyl, means carbon chains which may be linear or branched or combinations thereof. $C_{1-6}$, as in $C_{1-6}$alkyl is defined to identify the group as having 1, 2, 3, 4, 5 or 6 carbons in a linear or branched arrangement, such as methyl, ethyl, n-propyl, isopropyl, n-butyl, iso-butyl, sec-butyl, tert-butyl, pentyl, hexyl, and the like. "Alkylene" means a straight or branched chain of carbon atoms with a group substituted at both ends, such as —CH$_2$CH$_2$— and —CH$_2$CH$_2$CH$_2$—. "Alkenyl" means a carbon chain which contains at least one carbon-carbon double bond, and which may be linear or branched or combinations thereof such that $C_{2-6}$alkenyl is defined to identify the group as having 2, 3, 4, 5 or 6 carbons which incorporates at least one double bond, which may be in a E- or a Z-arrangement, including vinyl, allyl, isopropenyl, pentenyl, hexenyl, heptenyl, 1-propenyl, 2-butenyl, 2-methyl-2-butenyl, and the like. "Alkynyl" means a carbon chain which contains at least one carbon-carbon triple bond, and which may be linear or branched or combinations thereof, such as ethynyl, propargyl, 3-methyl-1-pentynyl, 2-heptynyl and the like. "Cycloalkyl" means a mono-, bi- or tri-cyclic structure, optionally combined with linear or branched structures, having the indicated number of carbon atoms, such as cyclopropyl, cyclopentyl, cycloheptyl, adamantyl, cyclododecylmethyl, 2-ethyl-1-bicyclo[4.4.0]decyl, and the like. "Alkoxy" means an alkoxy group of a straight or branched chain having the indicated number of carbon atoms. $C_{1-6}$alkoxy, for example, includes methoxy, ethoxy, propoxy, isopropoxy, and the like. The term "heterocyclyl" as used herein includes both unsaturated heterocyclic moieties comprising a mono- or bicyclic aromatic rings with at least one ring containing a heteroatom selected from N, O and S, and each ring containing 5 or 6 atoms (i.e. "heteroaryl") and saturated heterocyclic moieties comprising mono- or bicyclic saturated rings with at least one ring containing a heteroatom selected from N, O and S, and each ring containing 3, 5 or 6 atoms. Examples of "heteroaryl" include benzoimidazolyl, benzimidazolonyl, benzofuranyl, benzofurazanyl, benzopyrazolyl, benzothiazolyl, benzotriazolyl, benzothiophenyl, benzoxazepin, benzoxazolyl, carbazolyl, carbolinyl, cinnolinyl, furanyl, furo(2,3-b)pyridyl, imidazolyl, indolinyl, indolyl, dihydroindolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydroquinoxalinyl, tetrazolyl, tetrazolopyridyl, thiadiazolyl, thiazolyl, thienyl, triazolyl, and N-oxides thereof. Examples of saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

A group which is designated as being substituted with substituents may be substituted with multiple numbers of such substituents. A group which is designated as being independently substituted with substituents may be independently substituted with multiple numbers of such substituents.

The compounds of the present invention may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Examples of isotopes suitable for inclusion in the compounds of the invention include isotopes of hydrogen such as $^{2}H$ and $^{3}H$, carbon such as $^{11}C$, $^{13}C$ and $^{14}C$, nitrogen such as $^{13}N$ and $^{15}N$, oxygen such as $^{15}O$, $^{17}O$ and $^{18}P$, phosphorus such as $^{32}P$, sulfur such as $^{35}S$, fluorine such as $^{18}F$, iodine such as $^{23}I$ and $^{125}I$, and chlorine such as $^{36}Cl$. Certain isotopically-labelled compounds of Formula I, for example those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection. Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labelled compounds of Formula I can generally be prepared by conventional techniques known to those skilled in the art or by processes analogous to those described in the accompanying Examples using appropriate isotopically-labelled reagents in place of the non-labelled reagent previously employed.

It will be understood that, as used herein, references to the compounds of present invention are meant to also include the pharmaceutically acceptable salts, and also salts that are not pharmaceutically acceptable when they are used as precursors to the free compounds or in other synthetic manipulations. The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, cupric, cuprous, ferric, ferrous, lithium, magnesium, manganic, manganous, potassium, sodium, zinc and the like salts. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention are the specific compounds disclosed in the Examples and herein. The subject compounds are useful in a method of treating a neurological or psychiatric disorder associated with PDE10 dysfunction in a patient such as a mammal in need of such inhibition comprising the administration of an effective amount of the compound. In addition to primates, especially humans, a variety of other mammals can be treated according to the method of the present invention. The subject compounds are useful in a method of inhibiting PDE10 activity in a patient such as a mammal in need of such inhibition comprising the administration of an effective amount of the compound. The subject compounds are also useful for treating a neurological or psychiatric disorder associated with striatal hypofunction or basal ganglia dysfunction in a mammalian patient in need thereof. In addition to primates, especially humans, a variety of other mammals can be treated according to the method of the present invention.

The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for treating a neurological or psychiatric disorder associated with PDE10 dysfunction in a mammalian patient in need thereof. The present invention is further directed to a use of a compound of the present invention or a pharmaceutically acceptable salt thereof for the manufacture of a medicament for treating a neurological or psychiatric disorder associated with striatal hypofunction or basal ganglia dysfunction in a mammalian patient in need thereof.

"Treating" or "treatment of" a disease state includes: 1) preventing the disease state, i.e. causing the clinical symptoms of the disease state not to develop in a subject that may be exposed to or predisposed to the disease state, but does not yet experience or display symptoms of the disease state; 2) inhibiting the disease state, i.e., arresting the development of the disease state or its clinical symptoms; 3) or relieving the disease state, i.e., causing temporary or permanent regression of the disease state or its clinical symptoms.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy to retard the progression or reduce the risk of the noted conditions, particularly in a patient who is predisposed to such disease or disorder.

Applicants propose that inhibitors of PDE10 and, in particular inhibitors of PDE10A, will provide therapeutic benefit to those individuals suffering from psychiatric and cognitive disorders. The unique and exclusive distribution of PDE10A in the medium spiny projection neurons of the striatum, which form the principle site for cortical and dopaminergic input within basal ganglia, suggests that it may be possible and desirable to identify inhibitors of PDE10 to ameliorate or eliminate unwanted cellular signaling within this site. Without wishing to be bound by any theory, Applicants believe that inhibition of PDE10A in the striatum will result in increased cAMP/cGMP signaling and striatal output, which has the potential to restore behavioral inhibition that is impaired in cognitive disease such as schizophrenia. Regulation and integration of glutamatergic and dopaminergic inputs will enhance cognitive behavior, while suppressing or reducing unwanted behavior. Thus, in one embodiment, compounds of the invention provide a method for treating or ameliorating diseases or conditions in which striatal hypofunction is a prominent feature or ones in which basal ganglia dysfunction plays a role, such as, Parkinson's disease, Huntington's disease, schizophrenia, obsessive-compulsive disorders, addiction and psychosis. Other conditions for which the inhibitors described herein may have a desirable and useful effect include those requiring a reduction in activity and reduced response to psychomotor stimulants or where it would be desirable to reduce conditional avoidance responses, which is often predictive of clinical antipsychotic activity.

As used herein, the term "'selective PDE10 inhibitor" refers to an organic molecule that effectively inhibits an enzyme from the PDE10 family to a greater extent than enzymes from the PDE 1-9 or PDE11 families. In one embodiment, a selective PDE10 inhibitor is an organic molecule having a Ki for inhibition of PDE10 that is less than or about one-tenth that for a substance that is an inhibitor for another PDE enzyme. In other words, the organic molecule inhibits PDE 10 activity to the same degree at a concentration of about one-tenth or less than the concentration required for any other PDE enzyme. Preferably, a selective PDE10 inhibitor is an organic molecule, having a Ki for inhibition of PDE10 that is less than or about one-hundredth that for a substance that is an inhibitor for another PDE enzyme. In other words, the organic molecule inhibits PDE10 activity to the same degree at a concentration of about one-hundredth or less than the concentration required for any other PDE enzyme. A "selective PDE10 inhibitor" can be identified, for example, by comparing the ability of an organic molecule to inhibit PDE10 activity to its ability to inhibit PDE enzymes from the other PDE families. For example, an organic molecule may be assayed for its ability to inhibit PDE10 activity, as well as PDE1A, PDE1B, PDE1C, PDE2A, PDE3A, PDE3B, PDE4A, PDE4B, PDE4C, PDE4D, PDE5A, PDE6A, PDE6B, PDE6C, PDE7A, PDE7B, PDE8A, PDE8B, PDE9A, and/or PDE11A.

Phosphodiesterase enzymes including PDE10 have been implicated in a wide range of biological functions. This has suggested a potential role for these enzymes in a variety of disease processes in humans or other species. The compounds of the present invention have utility in treating a variety of neurological and psychiatric disorders.

In a specific embodiment, compounds of the present invention provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temporal dementia, delirium, amnestic disorders or age related cognitive decline.

In another specific embodiment, compounds of the present invention provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, compounds of the present invention provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-10 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with postpartum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder (PDD), mood disorders due to a general medical condition, and substance-induced mood disorders.

In another specific embodiment, compounds of the present invention provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other specific embodiments, compounds of the invention provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxysmal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy. Of the disorders above, the treatment of schizophrenia, bipolar disorder, depression, including unipolar depression, seasonal depression and post-partum depression, premenstrual syndrome (PMS) and premenstrual dysphoric disorder (PDD), learning disorders, pervasive developmental disorders, including autistic disorder, attention disorders including Attention-Deficit/Hyperactivity Disorder, autism, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

The activity of the compounds in accordance with the present invention as PDE10 inhibitors may be readily determined without undue experimentation using a fluorescence polarization (FP) methodology that is well known in the art (Huang, W., et al., *J. Biomol Screen*, 2002, 7: 215). In particular, the compounds of the following examples had activity in reference assays by exhibiting the ability to inhibit the hydrolysis of the phosphphate ester bond of a cyclic nucleotide. Any compound exhibiting a Ki (inhibitory constant) below 1 μM would be considered a PDE10 inhibitor as defined herein.

In a typical experiment the PDE10 inhibitory activity of the compounds of the present invention was determined in accordance with the following experimental method. PDE10A2 was amplified from human fetal brain cDNA (Clontech, Mountain View, Calif.) using a forward primer corresponding to nucleotides 56-77 of human PDE10A2 (Accession No. AF127480, Genbank Identifier 4894716), containing a Kozak consensus sequence, and a reverse primer corresponding to nucleotides 2406-2413 of human PDE10A2 (Accession No. AF127480, Genbank Identifier 4894716). Amplification with Easy-A polymerase (Stratagene, La Jolla, Calif.) was 95° C. for 2 minutes followed by thirty three cycles of 95° C. for 40 seconds, 55° C. for 30 seconds, and 72° C. for 2 minutes 48 seconds. Final extension was 72° C. for 7 minutes. The PCR product was TA cloned into pcDNA3.2-TOPO (Invitrogen, Carlsbad, Calif.) according to standard protocol. AD293 cells with 70-80% confluency were transiently transfected with human PDE10A2/pcDNA3.2-TOPO using Lipofectamine 2000 according to manufacturer specifications (Invitrogen, Carlsbad, Calif.). Cells were harvested 48 hours post-transfection and lysed by sonication (setting 3, 10×5 sec pulses) in a buffer containing 20 mM HEPES, 1 mM EDTA and protease inhibitor cocktail (Roche). Lysate was collected by centrifugation at 75,000×g for 20 minutes. Supernatant containing the cytoplasmic fraction was used for evaluation of PDE10A2 activity. The fluorescence polarization assay for cyclic nucleotide phosphodiesterases was performed using an IMAP® FP kit supplied by Molecular Devices, Sunnyvale, Calif. (product #R8139). IMAP® technology has been applied previously to phosphodiesterase assays (Huang, W., et al., *J. Biomol Screen*, 2002, 7: 215). Assays were performed at room temperature in 384-well microtiter plates with an incubation volume of 20.2 µl. Solutions of test compounds were prepared in DMSO and serially diluted with DMSO to yield 8 µL of each of 10 solutions differing by 3-fold in concentration, at 32 serial dilutions per plate. 100% inhibition is determined using a known PDE10 inhibitor, which can be any compound that is present at 5,000 times its Ki value in the assay described as follows, such as papaverine (see Siuciak, et al. *Neuropharmacology* (2006) 51:386-396; Becker, et al. *Behav Brain Res* (2008) 186(2):155-60; Threlfell, et al., *J Pharmacol Exp Ther* (2009) 328(3):785-795), 2-{4-[pyridin-4-yl-1-(2,2,2-trifluoroethyl)-1H-pyrazol-3-yl]phenoxymethyl}quinoline succinic acid or 2-[4-(1-methyl-4-pyridin-4-yl-1H-pyrazol-3-yl)-phenoxymethyl]quinoline succinic acid (see Schmidt, et al. *J Pharmacol Exp Ther* (2008) 325:681-690; Threlfell, et al., *J Pharmacol Exp Ther* (2009) 328(3): 785-795). 0% of inhibition is determined by using DMSO (1% final concentrations).

A Labcyte Echo 555 (Labcyte, Sunnyvale, Calif.) is used to dispense 200 nL from each well of the titration plate to the 384 well assay plate. A solution of enzyme (1/1600 dilution from aliquots; sufficient to produce 20% substrate conversion) and a separate solution of FAM-labeled cAMP PDE from Molecular Devices (product #R7506), at a final concentration of 50 nM are made in the assay buffer (10 mM Tris HCl, pH 7.2, 10 mM $MgCl_2$, 0.05% $NaN_3$ 0.01% Tween-20, and 1 mM DTT). The enzyme and the substrate are then added to the assay plates in two consecutive additions of 10 µL, and then shaken to mix. The reaction is allowed to proceed at room temperature for 30 minutes. A binding solution is then made from the kit components, comprised of 80% Solution A, 20% Solution B and binding reagent at a volume of 1/600 the total binding solution. The enzymatic reaction is stopped by addition of 60 µL of the binding solution to each well of the assay plates and the plates are sealed and shaken for 10 seconds. The plate was incubated at room temperature for at least one hour prior to determining the fluorescence polarization (FP). The parallel and perpendicular fluorescence of each well of the plate was measured using a Perkin Elmer Enyision™ plate reader (Waltham, Mass.).

Fluorescence polarization (mP) was calculated from the parallel (S) and perpendicular (P) fluorescence of each sample well and the analogous values for the median control well, containing only substrate (So and Po), using the following equation:

Polarization($mP$)=1000*($S/So-P/Po$)/($S/So+P/Po$).

Dose-inhibition profiles for each compound were characterized by fitting the mP data to a four-parameter equation given below. The apparent inhibition constant ($K_I$), the maximum inhibition at the low plateau relative to "100% Inhibition Control" (Imax; e.g. 1=>same as this control), the minimum inhibition at the high plateau relative to the "0% Inhibition Control" (Imin, e.g. 0=>same as the no drug control) and the Hill slope (nH) are determined by a non-linear least squares fitting of the mP values as a function of dose of the compound using an in-house software based on the procedures described by Mosser et al., *JALA*, 2003, 8: 54-63, using the following equation:

$$mP = \frac{(0\% \ mP - 100\% \ mP)(Imax - Imin)}{1 + \left[\frac{[Drug]}{\left(10^{-pK_I}\left(1 + \frac{[Substrate]}{K_M}\right)\right)}\right]^{nH}} +$$

$$100\% \ mP + (0\% \ mP - 100\% \ mP)(1 - Imax)$$

The median signal of the "0% inhibition controls" (0% mP) and the median signal of the "100% inhibition controls" (100% mP) are constants determined from the controls located in columns 1-2 and 23-24 of each assay plate. An apparent ($K_m$) for FAM-labeled cAMP of 150 nM was determined in separate experiments through simultaneous variation of substrate and selected drug concentrations.

Selectivity for PDE10, as compared to other PDE families, was assessed using the IMAP® technology. Rhesus PDE2A3 and Human PDE10A2 enzyme was prepared from cytosolic fractions of transiently transfected HEK cells. All other PDE's were GST Tag human enzyme expressed in insect cells and were obtained from BPS Bioscience (San Diego, Calif.): PDE1A (Cat #60010), PDE3A (Cat #60030), PDE4A1A (Cat #60040), PDE5A1 (Cat #60050), PDE6C (Cat #60060), PDE7A (Cat #60070), PDE8A1 (Cat #60080), PDE9A2 (Cat #60090), PDE11A4 (Cat #60110).

Assays for PDE 1 through 11 were performed in parallel at room temperature in 384-well microtiter plates with an incubation volume of 20.2 µL. Solutions of test compounds were prepared in DMSO and serially diluted with DMSO to yield 30 µL of each of ten solutions differing by 3-fold in concentration, at 32 serial dilutions per plate. 100% inhibition was determined by adding buffer in place of the enzyme and 0% inhibition is determined by using DMSO (1% final concentrations). A Labcyte POD 810 (Labcyte, Sunnyvale, Calif.) was used to dispense 200 nL from each well of the titration plate to make eleven copies of the assay plate for each titration, one copy for each PDE enzyme. A solution of each enzyme (dilution from aliquots, sufficient to produce 20% substrate conversion) and a separate solution of FAM-labeled cAMP or FAM-labeled cGMP from Molecular Devices (Sunnyvale, Calif., product #R7506 or cGMP #R7508), at a final concentration of 50 nM were made in the assay buffer (10 mM Tris HCl, pH 7.2, 10 mM $MgCl_2$, 0.05% $NaN_3$ 0.01% Tween-20, and 1 mM DTT). Note that the substrate for PDE2 is 50 nM FAM cAMP containing 1000 nM of cGMP. The enzyme and the substrate were then added to the assay plates in two consecutive additions of 10 µL and then shaken to mix. The reaction was allowed to proceed at room temperature for 60 minutes. A binding solution was then made from the kit components, comprised of 80% Solution A, 20% Solution B and binding reagent at a volume of 1/600 the total binding solution. The enzymatic reaction was stopped by addition of 60 µL of the binding solution to each well of the assay plate. The plates were sealed and shaken for 10 seconds. The plates were incubated at room temperature for one hour, then the parallel and perpendicular fluorescence was measured using a Tecan Genios Pro plate reader (Tecan, Switzerland). The apparent inhibition constants for the compounds against all 11 PDE's was determined from the parallel and perpendicular fluorescent readings as described for PDE10 FP assay using the following apparent $K_M$ values for each enzyme and substrate combination: PDE1A (FAM cGMP) 70 nM, rhesus PD2A3 (FAM cAMP) 10,000 nM, PDE3A (FAM cAMP) 50 nM, PDE4A1A (FAM cAMP) 1500 nM, PDE5A1 (FAM cGMP) 400 nM, PDE6C (FAM cGMP) 700 nM, PDE7A (FAM cAMP) 150 nM, PDE8A1 (FAM cAMP) 50 nM, PDE9A2 (FAM cGMP) 60 nM, PDE10A2 (FAM cAMP) 150 nM, PDE11A4 (FAM cAMP) 1000 nM. The intrinsic PDE10 inhibitory activity of a compound which may be used in accordance with the present invention may be determined by these assays.

The compounds of the following examples had activity in inhibiting the human PDE 10 enzyme in the aforementioned assays, generally with an Ki of less than about 1 µM. Many of compounds within the present invention had activity in inhibiting the human PDE 10 enzyme in the aforementioned assays, generally with an Ki of less than about 0.1 µM. Additional data is provided in the following Examples. Such a result is indicative of the intrinsic activity of the compounds in use as inhibitors of the PDE10 enzyme. In general, one of ordinary skill in the art would appreciate that a substance is considered to effectively inhibit PDE10 activity if it has a Ki of less than or about 1 µM, preferably less than or about 0.1 µM. The present invention also includes compounds within the generic scope of the invention which possess activity as inhibitors of other phosphodiesterase enzymes.

The subject compounds are further useful in a method for the prevention, treatment, control, amelioration, or reduction of risk of the diseases, disorders and conditions noted herein. The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with thesubject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, $5\text{-HT}_{1A}$ agonists or antagonists, especially $5\text{-HT}_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg. of body weight daily are administered to the patient, e.g., humans and elderly humans. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Several methods for preparing the compounds of this invention are illustrated in the following Schemes and Examples. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; Ac: acetyl; THF: tetrahydrofuran; Boc: tert-butyloxycarbonyl; DIPEA: N,N-diisopropylethylamine; DPPA: diphenylphosphorylazide; EDC: N-(3-Dimethylaminopropyl)-N'-ethylcarbodiimide; EtOAc: ethyl acetate; HOBt: hydroxybenzotriazole hydrate; TEA: triethylamine; DMF: N,N-dimethylformamide; rt: room temperature; HPLC: high performance liquid chromatography; NMR: nuclear magnetic resonance; TLC: thin-layer chromatography. The compounds of the present invention can be prepared in a variety of fashions.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

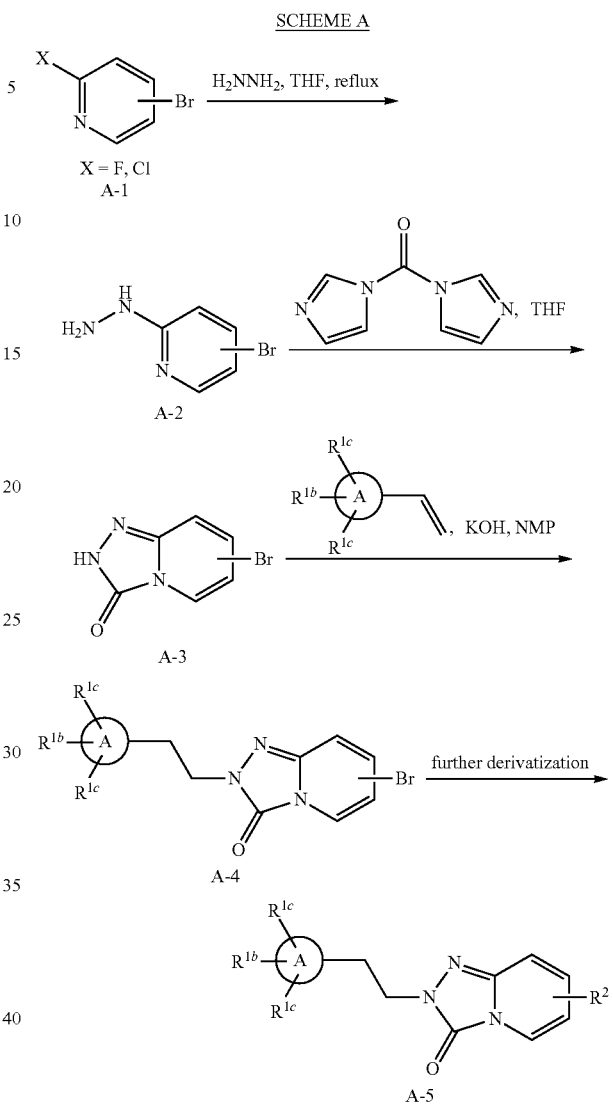

As depicted in Scheme A, a 2-halopyridine (A-1) is reacted with hydrazine to produce aryl hydrazine A-2. The aryl hydrazine is treated with carbonyldiimidazole (CDI) to give the triazolopyridinone core A-3. The triazolopyridinone is then made to undergo conjugate addition to a vinyl-substituted heterocycle under basic conditions, yielding subject compounds A-4. A reactive handle on the triazolopyridinone, such as bromine, is further modified by, for example, a cross-coupling reaction, to provide subject compounds A-5.

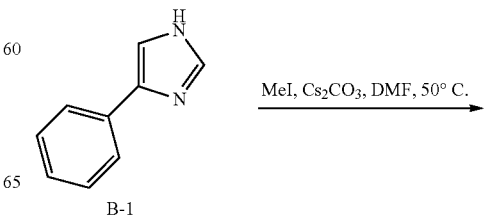

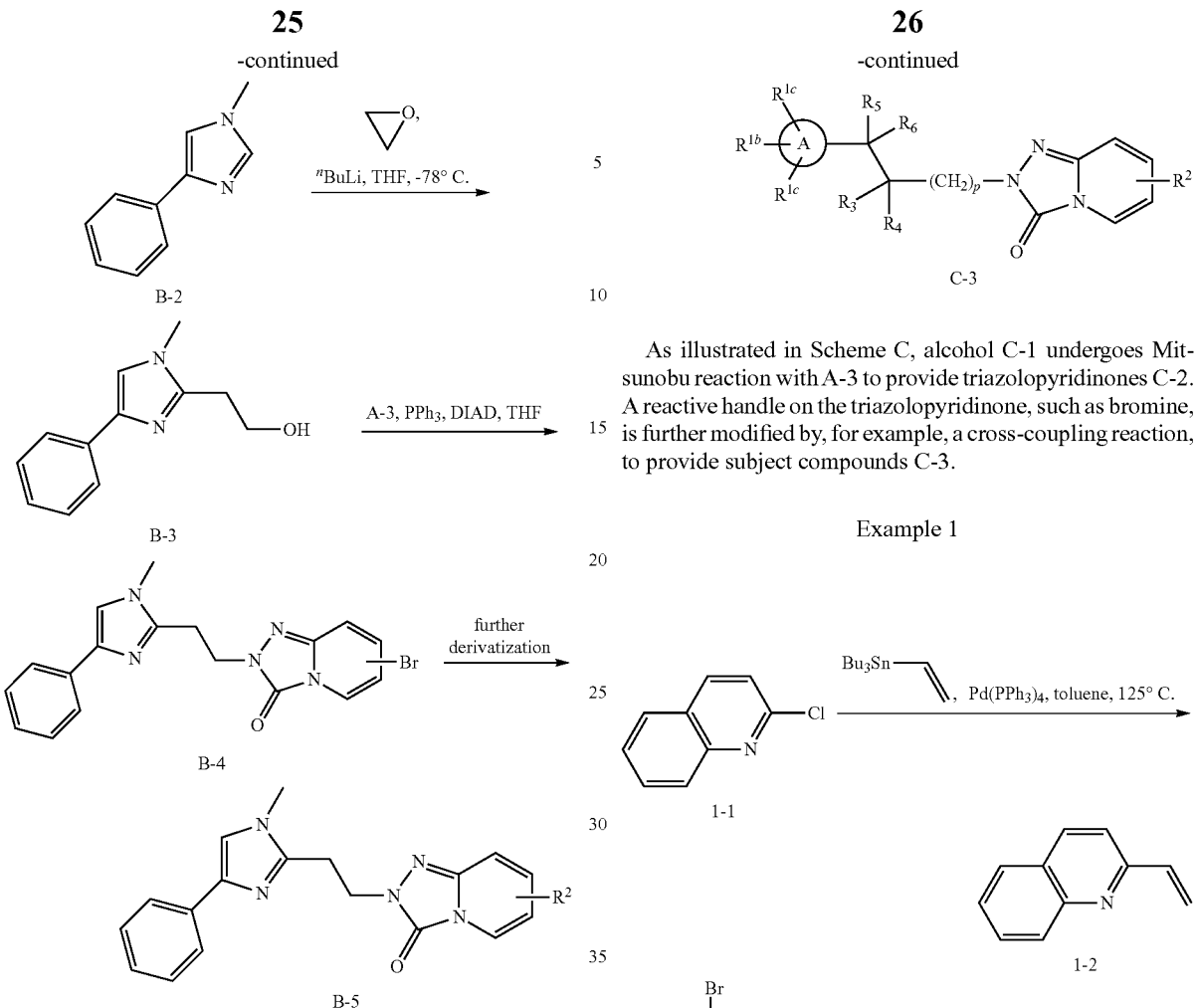

As illustrated in Scheme C, alcohol C-1 undergoes Mitsunobu reaction with A-3 to provide triazolopyridinones C-2. A reactive handle on the triazolopyridinone, such as bromine, is further modified by, for example, a cross-coupling reaction, to provide subject compounds C-3.

Example 1

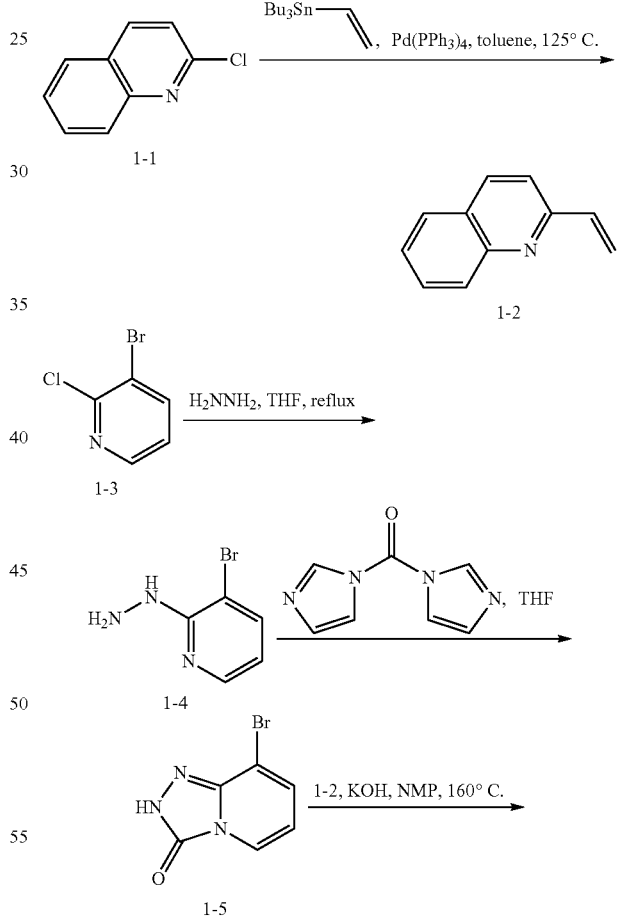

As shown in Scheme B, 4-phenylimidazole (B-1) is treated with iodomethane under basic conditions to afford B-2. On deprotonation with n-butyllithium, B-2 reacts with oxirane to produce alcohol B-3, which can be elaborated to subject compounds B-4 under Mitsunobu reaction conditions in the presence of triazolopyridinone A-3. A reactive handle on the triazolopyridinone, such as bromine, is further modified by, for example, a nucleophilic aromatic substitution reaction, to provide subject compounds B-5.

SCHEME C

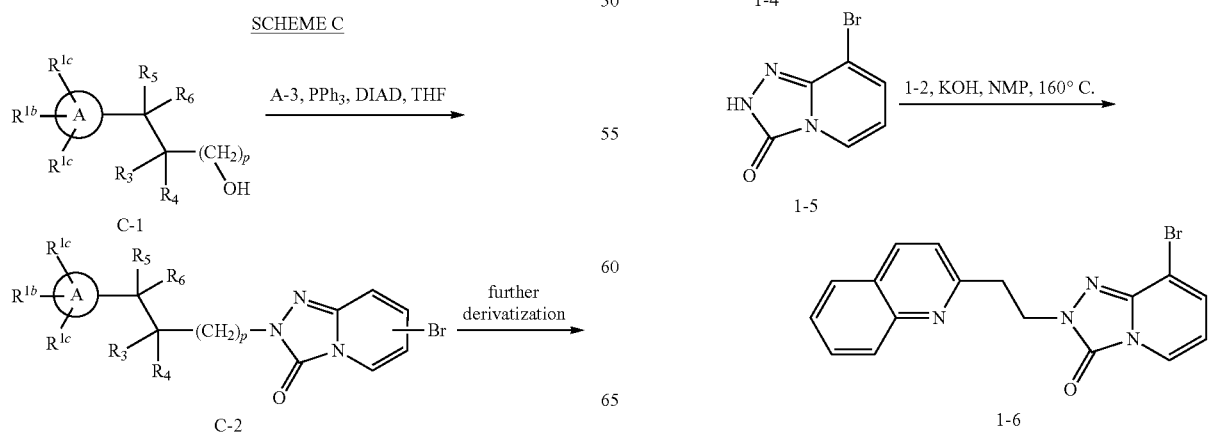

2-vinylquinoline (1-2)

2-chloroquinoline (1-1) (1.00 g, 6.1 mmol) in toluene (25 mL) was sparged with $N_2$ gas for 5 min, and tributyl(vinyl) stannane (2.52 g, 2.33 mL, 8.0 mmol) and tetrakis(triphenylphosphine)palladium (0.353 g, 0.31 mmol) were added. The mixture was heated at 125° C. for 1 h, then cooled and concentrated in vacuo. The residue was suspended in $CH_2Cl_2$ (20 mL) and purified by silica gel flash column chromatography (80 g cartridge), eluting with 0-30% EtOAc/hexanes over 20 min. The fractions containing the desired product (1-2) were pooled, and after solvent removal in vacuo, 700 mg (74%) of a clear oil were obtained. LC/MS: m/z (M+H)=156.0.

3-bromo-2-hydrazinylpyridine (1-4)

To 3-bromo-2-chloropyridine (1-3) (12.5 g, 65 mmol) in THF (100 mL) was added hydrazine (10.4 g, 10.2 mL, 325 mmol). The mixture was heated to reflux and stirred vigorously for 16 h. An additional portion of hydrazine (5.1 g, 5.0 mL, 159 mmol) was added and the reaction was heated for another 24 h. After cooling, the mixture was concentrated in vacuo, suspended in water (50 mL), and extracted with EtOAc (1×350 mL, 1×50 mL). Combined organic layers were washed with brine (50 mL), dried over $MgSO_4$, filtered, and concentrated in vacuo. The resulting crude product (1-4) was used in the subsequent step without further purification. LC/MS: m/z (M+H)=187.9.

8-bromo-[1,2,4]triazolo[4,3-a]pyridin-3(2H)-one (1-5)

To a solution of 1-4 (5.0 g, 26.6 mmol) in THF (50 mL) was added carbonyldiimidazole (5.61 g, 34.6 mmol), and the heterogeneous mixture was stirred for 2 h. The reaction was diluted with water (150 mL) and EtOAc (150 mL), causing a precipitate to form. The mixture was filtered through a sintered glass filter, yielding 2.0 g (35%) of 1-5 as a tan solid. $^1H$ NMR (300 MHz, DMSO-$d_6$) δ 12.73 (s, 1H), 7.88 (dd, J=7.2, 0.9 Hz, 1H), 7.58 (dd, J=7.2, 0.9 Hz, 1H), 6.51 (app t, J=7.2 Hz, 1H).

8-bromo-2-(2-(quinolin-2-yl)ethyl)-[1,2,4]triazolo[4,3-a]pridin-3(2H)-one (1-6)

2-Vinylquinoline (1-2) (218 mg, 1.40 mmol) and triazolopyridinone 1-5 (250 mg, 1.17 mmol) were placed in a microwave vial and dissolved in NMP (3 mL). To the mixture was added catalytic powdered KOH (13 mg, 0.234 mmol), and the vial was capped and heated at 160° C. under microwave irradiation for 20 min. After cooling, the mixture was diluted with $CH_2Cl_2$ (100 mL) and washed with water (25 mL) and brine (25 mL). The organic layer was dried over $MgSO_4$, filtered, and concentrated in vacuo. The crude material was purified by silica gel flash column chromatography (40 g cartridge), eluting with 20-100% EtOAc/hexanes. The fractions containing the desired product (1-6) were pooled, and after solvent removal in vacuo, 240 mg (52%) of a fluffy yellow solid were obtained. $^1H$ NMR (300 MHz, CHCl$_3$-d) δ 8.07 (d, J=8.4 Hz, 1H), 8.02 (d, J=8.5 Hz, 1H), 7.77 (app t, J=8.0 Hz, 2H), 7.68 (t, J=7.7 Hz, 1H), 7.50 (t, J=7.5 Hz, 1H), 7.38-7.30 (m, 2H), 6.39 (dd, J=7.2, 6.7 Hz, 1H), 4.61 (t, J=7.6 Hz, 2H), 3.57 (t, J=7.6 Hz, 2H); HRMS (ES) 369.0345 (M+H) found, 369.0349 required.

Example 2

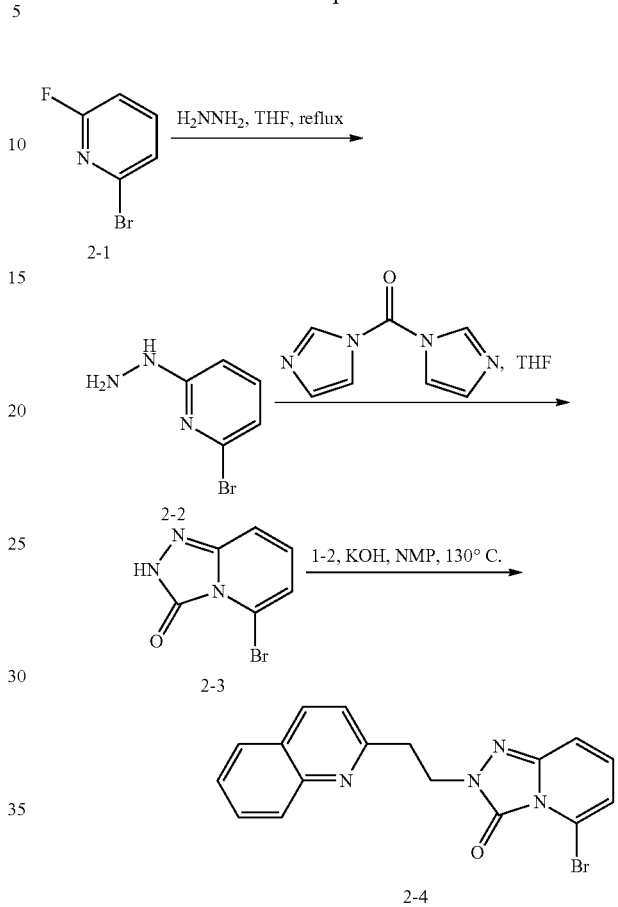

2-bromo-6-hydrazinylpyridine (2-2)

To a solution of 2-bromo-6-fluoropyridine (2-1) (1.0 g, 5.68 mmol) in THF (10 mL) was added hydrazine (0.91 g, 0.89 mL, 28.4 mmol). After stirring for 1 h room temperature, the mixture was heated at 65° C. for 1 h. The mixture was cooled, diluted with EtOAc (200 mL), washed with water (10 mL) and brine (10 mL), dried over $MgSO_4$, filtered, and concentrated in vacuo. The resulting crude product (2-2) was used in the subsequent step without further purification. $^1H$ NMR (300 MHz, CHCl$_3$-d): δ 7.32 (app t, J=7.8 Hz, 1H), 6.82 (dd, J=7.8, 0.6 Hz, 1H), 6.67 (dd, J=7.8, 0.6 Hz, 1H), 5.93 (s, 1H), 3.80 (s, 2H).

5-bromo-[1,2,4]triazolo[4,3-a]pyridin-3(2H)-one (2-3)

To a solution of 2-2 (1.1 g, 5.85 mmol) in THF (50 mL) was added carbonyldiimidazole (1.14 g, 7.02 mmol), and the mixture was stirred for 1 h. The reaction was diluted with water (150 mL) and EtOAc (150 mL), causing a precipitate to form. The mixture was filtered through a sintered glass filter, yielding 0.8 g (64%) of 2-3 as a tan solid. $^1H$ NMR (300 MHz, CHCl$_3$-d) δ 9.34 (s, 1H), 7.03 (m, 1H), 6.85 (m, 1H), 6.59 (m, 1H).

5-bromo-2-(2-(quinolin-2-yl)ethyl)-[1,2,4]triazolo[4,3-a]pyridin-3(2H)-one (2-4)

2-Vinylquinoline (1-2) (218 mg, 1.40 mmol) and triazolopyridinone 2-3 (250 mg, 1.17 mmol) were placed in a microwave vial and dissolved in NMP (2 mL). To the mixture was added catalytic powdered KOH (10 mg, 0.18 mmol), and the vial was capped and heated at 130° C. under microwave irradiation for 20 min. After cooling, the mixture was diluted with CH$_2$Cl$_2$ (100 mL) and washed with water (25 mL) and brine (25 mL). The organic layer was dried over MgSO$_4$, filtered, and concentrated in vacuo. The crude material was purified by silica gel flash column chromatography (40 g cartridge), eluting with 25-100% EtOAc/hexanes. The fractions containing the desired product (2-4) were pooled, and after solvent removal in vacuo, 40 mg (9%) of a white solid were obtained. $^1$H NMR (400 MHz, CHCl$_3$-d): δ 8.08 (d, J=8.4 Hz, 1H), 8.03 (d, J=8.4 Hz, 1H), 7.78 (d, J=8.0 Hz, 1H), 7.69 (m, 1H), 7.50 (app t, J=7.6 Hz, 1H) 7.32 (d, J=8.8 Hz, 1H), 7.00 (d, J=11.6 Hz, 1H), 6.81 (dd, J=9.6, 7.2 Hz, 1H), 6.57 (d, J=7.2 Hz, 1H), 4.51 (t, J=7.2 Hz, 2H), 3.52 (t, J=7.2 Hz, 2H). HRMS (ES) 369.0346 (M+H) found, 369.0349 required.

Example 3

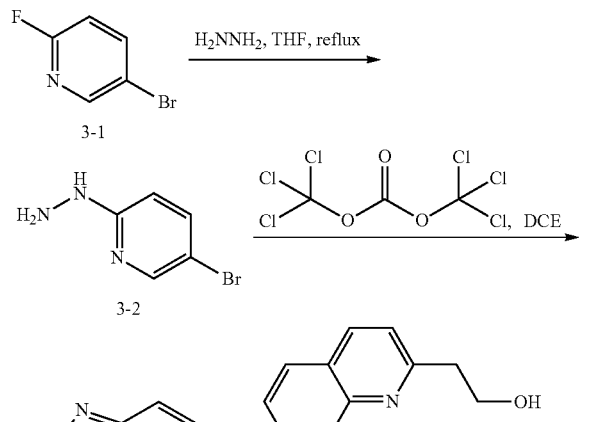

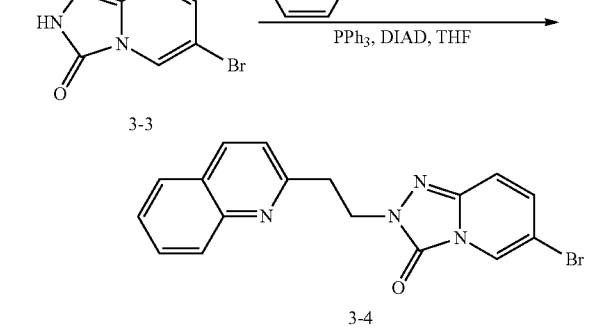

5-bromo-2-hydrazinylpyridine (3-2)

To 5-bromo-2-fluoropyridine (3-1) (46 g, 261 mmol) in THF (460 mL) was added hydrazine (41.9 g, 41.0 mL, 1.31 mol). The mixture was heated to reflux and stirred vigorously for 2 h. After cooling, the reaction mixture was diluted with water (200 mL) and extracted with EtOAc (3×500 mL). The combined organic layers were washed with brine, dried over MgSO4, filtered, and concentrated in vacuo. The resulting crude product (3-2) was used in the subsequent step without further purification. LC/MS: m/z (M+H)=187.9.

6-bromo-[1,2,4]triazolo[4,3-a]pyridin-3(2H)-one (3-3)

To a solution of 3-2 (2.0 g, 10.6 mmol) in dichloroethane (106 mL) was added triphosgene (3.16 g, 10.64 mmol). The reaction mixture was stirred at room temperature for 3 days. An off-white precipitate formed, which was washed with dichloroethane (100 mL) and dried in vacuo to give 2.03 g (89%) of 3-3 as a tan solid. LC/MS: m/z (M+H)=213.9.

6-bromo-2-(2-(quinolin-2-yl)ethyl)-[1,2,4]-triazolo[4,3-a]pyridin-3(2H)-one (3-4)

In a 1-dram vial were placed 2-(quinolin-2-yl)ethanol (405 mg, 2.80 mmol), DIAD (472 mg, 2.34 mmol) and triphenylphosphine (613 mg, 2.34 mmol) in THF (11.7 mL). The mixture was stirred at room temperature for 10 min, and 3-3 (600 mg, 2.80 mmol) was added in one portion. The reaction was further stirred for 10 min. The crude product was dried under stream of N$_2$ and purified by reversed phase HPLC to give 480 mg (55%) of 3-4. HRMS (ES) 369.0348 (M+H) found, 369.0349 required.

Example 4

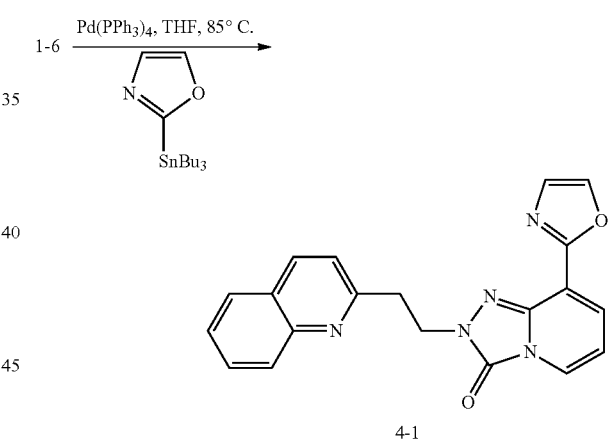

8-(oxazol-2-yl)-2-(2-(quinolin-2-yl)ethyl)-[1,2,4]triazolo[4,3-a]pyridin-3(2H)-one (4-1)

A solution of bromide 1-6 (43 mg, 0.116 mmol) in THF (2 mL) in a microwave vial was sparged with N$_2$ gas for 5 min, and 2-(tributylstannyl)oxazole (83 mg, 0.233 mmol) and tetrakis(triphenylphosphine)palladium (13 mg, 0.012 mmol) were added. The vial was capped and heated at 125° C. under microwave irradiation for 20 min, then another 30 min at 130° C. An additional portion of 2-(tributylstannyl)oxazole (50 mg, 0.140 mmol) was added, and the vial was heated at 85° C. in an oil bath for 16 h. After cooling, the reaction mixture was directly purified by silica gel flash column chromatography (12 g cartridge), eluting with 40-100% EtOAc/hexanes then 2% EtOH/EtOAc. The fractions containing the desired product (4-1) were pooled, and after solvent removal in vacuo, 6.8 mg (16%) of a yellow solid were obtained. $^1$H NMR (300

MHz, CHCl₃-d): δ 8.07 (d, J=8.4 Hz, 1H), 8.02 (d, J=7.8 Hz, 1H), 7.92 (dd, J=6.9, 1.2 Hz, 1H), 7.88 (dd, 6.9, 1.2 Hz, 1H), 7.80 (d, J=0.6 Hz, 1H), 7.78 (d, J=8.1 Hz, 1H), 7.68 (ddd, J=8.4, 7.2, 1.5 Hz, 1H), 7.50 (ddd, Jr=7.8, 6.6, 1.2 Hz, 1H), 7.35 (s, 1H), 7.33 (s, 1H), 6.64 (t, J=7.2 Hz, 1H), 4.69 (t, J=7.5 Hz, 2H), 3.61 (t, J=7.5 Hz, 2H). HRMS (ES) 358.1299 (M+H) found, 358.1302 required.

Example 5

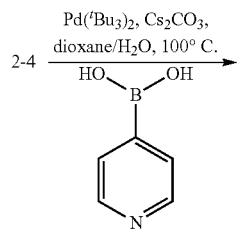

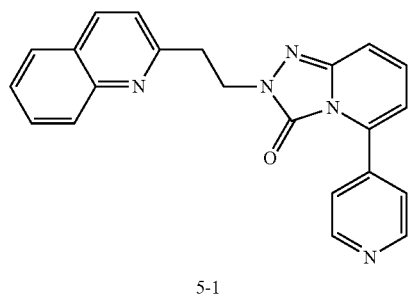

5-1

5-(pyridin-4-yl)-2-(2-(quinolin-2-yl)ethyl)-[1,2,4]triazolo[4,3-a]pyridin-3(2H)-one (5-1)

Triazolopyridinone 2-4 (40 mg, 0.11 mmol) and pyridin-4-ylboronic acid (27 mg, 0.22 mmol) were placed in a microwave vial and dissolved in dioxane (1 mL). To the mixture was added 1 M aq. Cs₂CO₃ solution (0.22 mL, 0.22 mmol). The mixture was then sparged with N₂ gas for 3 min, and bis(tri-tert-butylphosphine)palladium (5.5 mg, 0.011 mmol) was added. The vial was capped and heated at 100° C. under microwave irradiation for 30 min. After cooling, the reaction mixture was diluted with EtOAc (100 mL), washed with water (30 mL) and brine (30 mL), dried over MgSO₄, filtered, and concentrated in vacuo. The residue was purified by silica gel flash column chromatography (12 g cartridge), eluting with 0-10% MeOH/CH₂Cl₂. The fractions containing the desired product (5-1) were pooled, and after solvent removal in vacuo, 8.0 mg (20%) of a yellow solid were obtained. ¹H NMR (400 MHz, CHCl₃-d): δ 8.63 (dd, J=4.9, 1.5 Hz, 2H), 8.07 (d, J=8.4 Hz, 1H), 7.99 (d, J=8.4 Hz, 1H), 7.79 (d, J=8.0 Hz, 1H), 7.68 (ddd, J=8.4, 6.8, 1.6 Hz, 1H), 7.53-7.48 (m, 1H), 7.31 (d, J=8.4 Hz, 1H), 7.26 (d, J=6.0 Hz, 2H), 7.16 (d, J=9.6 Hz, 1H), 7.08 (dd, J=9.6, 6.4 Hz, 1H), 6.36 (d, J=6.4 Hz, 1H), 4.49 (t, J=7.2 Hz, 2H), 3.51 (t, J=7.2 Hz, 2H). HRMS (ES) 368.1508 (M+H) found, 368.1509 required.

Example 6

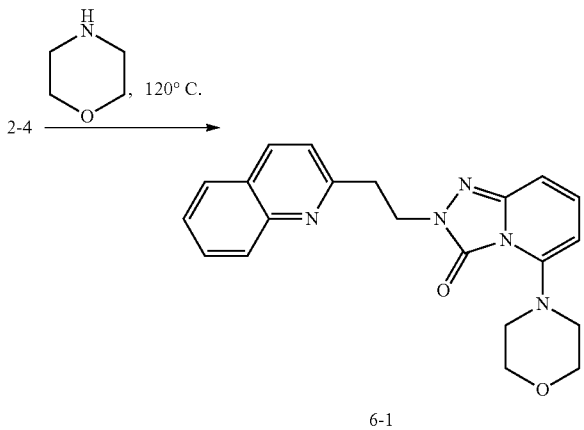

6-1

5-morpholino-2-(2-(quinolin-2-yl)ethyl)-[1,2,4]triazolo[4,3-a]pyridin-3(2H)-one (6-1)

In a 5 mL microwave vial was placed 2-4 (221 mg, 0.599 mmol) and morpholine (2.0 g, 2.0 mL, 23 mmol). The mixture was heated at 120° C. under microwave irradiation for 20 min. After cooling, the reaction mixture was purified by reversed phase HPLC to give 191 mg (85%) of 6-1. ¹H NMR (500 MHz, DMSO-d₆): δ 8.51 (d, J=8.2 Hz, 1H), 8.05 (d, J=8.2 Hz, 1H), 7.96 (d, J=8.5 Hz, 1H), 7.83 (t, J=7.7 Hz, 1H), 7.69-7.60 (m, 2H), 7.00 (t, J=8.1 Hz, 1H), 6.67 (d, J=9.3 Hz, 1H), 5.72 (d, J=7.0 Hz, 1H), 4.32 (t, J=7.0 Hz, 2H), 3.63 (m, 4H), 3.10 (s, 1H), 2.99 (s, 1H), 2.93 (s, 4H). HRMS (ES) 376.1765 (M+H) found, 376.1771 required.

Example 7

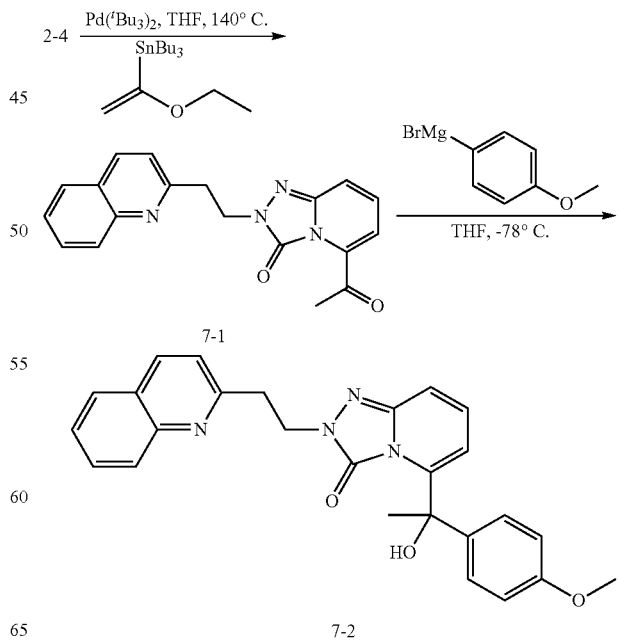

5-acetyl-2-(2-(quinolin-2-yl)ethyl)-[1,2,4]triazolo[4,3-a]pyridin-3(2H)-one (7-1)

In a 20 mL microwave vial were placed 2-4 (327 mg, 0.886 mmol), tributyl(1-methoxyvinyl)stannane (0.640 g, 1.771 mmol), and bis(tri-tert-butylphosphine)palladium (45 mg, 0.089 mmol) in THF (8.8 mL). The vial was sealed and the reaction was heated at 140° C. under microwave irradiation for 15 min. The reaction mixture was directly purified by silica gel flash column chromatography (100 g cartridge), eluting with 0-90% 1:1 EtOAc/(20:1:1 EtOH/NH$_4$OH/H$_2$O)/hexanes. The fractions containing the desired product (7-1) were pooled, and after solvent removal in vacuo, 310 mg of enol ether were obtained. This intermediate was placed in 20 mL scintillation vial, suspended in anhydrous diethyl ether, treated with 1 N HCl in diethyl ether, and stirred for 1 h at room temperature. The suspension was filtered to obtain 7-1 as a bright yellow solid, which was used in the subsequent step without further purification. LC/MS: m/z (M+H)=333.1.

5-(2-hydroxy-1-(4-methoxyphenyl)propan-2-yl)-2-(2-(quinolin-2-yl)ethyl)-[1,2,4]triazolo[4,3-a]pyridin-3(2H)-one (7-2)

In a flame-dried, 5 mL microwave vial was placed 7-1 (20 mg, 0.054 mmol) in THF (0.54 mL) under dry N$_2$ gas. The reaction mixture was cooled to −78° C., and a 0.5 M solution of (4-methoxyphenyl)magnesium bromide in THF (0.119 mmol, 0.24 mL) was added. After stirring for 15 min, the reaction was quenched with sat. aq. NH$_4$Cl (0.25 mL) and diluted with CH$_2$Cl$_2$ (2 mL). The mixture was transferred to a phase separator column, and the organic layer was collected and dried under a stream of N$_2$ gas. The crude product was purified by reversed phase HPLC (eluting with 20-60% acetonitrile/water with 0.1% NH$_4$OH modifier). Pure fractions were pooled and dried to give 6.3 mg (26%) of 7-2. HRMS (ES) 441.1911 found (M+H) found, 441.1923 required.

Example 8

3-oxo-2-(2-(quinolin-2-yl)ethyl)-2,3-dihydro-[1,2,4]triazolo[4,3-a]pyridine-5-carboxylic acid (8-1)

In a flame-dried, 5 mL microwave vial was placed 2-4 (199 mg, 0.54 mmol) in anhydrous THF (2.5 mL) under dry N$_2$ gas.

The reaction mixture was cooled to −78° C. and a 1.6 M solution of n-butyllithium in hexanes (0.371 mL, 0.59 mmol) was added dropwise. After stirring for 10 min at −78° C., dry CO$_2$ gas was bubbled through the solution for 2 min. The reaction was quenched with sat. aq. NH$_4$Cl, allowed to warm to room temperature, and then extracted with EtOAc (2×10 mL). The combined organic layers were concentrated in vacuo. The crude product was triturated with hexanes and CH$_2$Cl$_2$, then filtered to give 97 mg (54%) of 8-1 as a pink solid. The material was used in the subsequent step without further purification. LC/MS: m/z (M+H)=335.1.

3-oxo-N-(pyridin-3-yl)-2-(2-(quinolin-2-yl)ethyl)-2,3-dihydro-[1,2,4]triazolo[4,3-a]pyridine-5-carboxamide (8-2)

In a 1-dram vial was placed 8-1 (15 mg, 0.045 mmol) in anhydrous DMF (0.45 mL). To this solution was added EDC (8.0 mg, 0.045 mmol), HOAT (6.0 mg, 0.045 mmol), diisopropylethylamine (0.008 mL, 0.045 mmol), and 3-aminopyridine (0.001 g, 0.049 mmol). The reaction mixture was heated at 40° C. and stirred for 16 h. The crude reaction mixture was then directly purified by reversed phase HPLC to give 15.0 mg (80%) of 8-2. $^1$H NMR (500 MHz, DMSO-d$_6$): δ 11.06 (s, 1H), 8.84 (s, 1H), 8.44 (d, J=8.8 Hz, 1H), 8.40 (d, J=5.0 Hz, 1H), 8.14 (d, J=8.4 Hz, 1H), 8.00 (d, J=8.0 Hz, 1H), 7.95 (d, J=8.6 Hz, 1H), 7.79 (t, J=7.4 Hz, 1H), 7.64-7.55 (m, 2H), 7.53 (t, J=6.5 Hz, 1H), 7.32 (d, J=9.3 Hz, 1H), 7.24 (t, J=7.9 Hz, 1H), 6.85 (d, J=6.5 Hz, 1H), 4.39 (t, J=7.6 Hz, 2H), 3.46 (t, J=7.6 Hz, 2H). HRMS (ES) 411.1546 (M+H) found, 411.1567 required.

Example 9

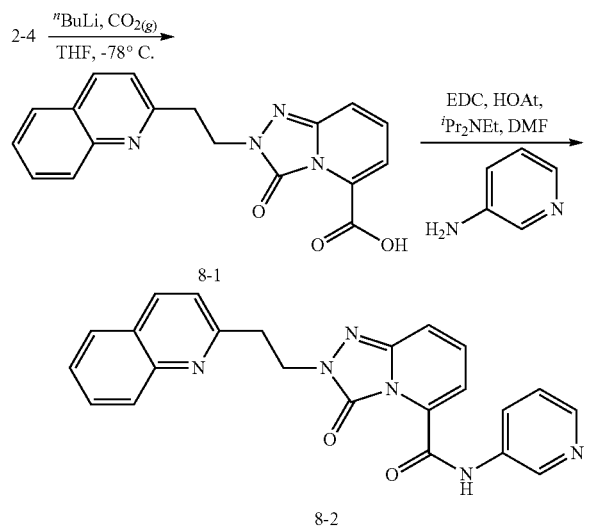

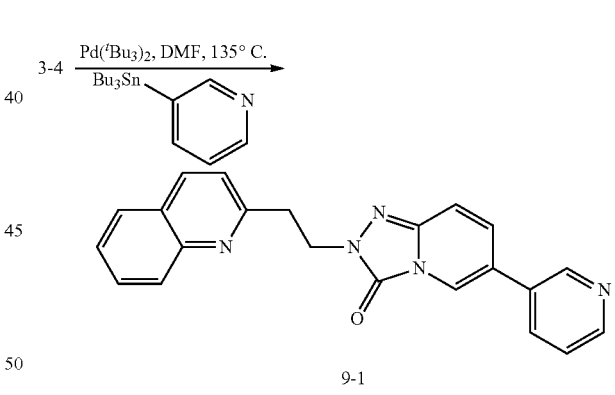

6-pyridin-3-yl-2-(2-(quinolin-2-ylethyl)[1,2,4]triazolo[4,3-a]pyridin-3(2H)-one (9-1)

In a 2 mL microwave vial were placed 3-4 (15 mg, 0.041 mmol), 3-(tributylstannyl)pyridine (16 mg, 0.045 mmol), and bis(tri-tert-butylphosphine)palladium (2 mg, 0.004 mmol) in anhydrous DMF (0.4 mL). The vial was sealed and the reaction was heated at 135° C. under microwave irradiation for 15 min. The reaction mixture was filtered, and the filtrate was directly purified by reversed phase HPLC to give 5.0 mg (35%) of 9-1. $^1$H NMR (500 MHz, DMSO-d$_6$): δ 9.03 (s, 1H), 8.67 (d, J=5.0 Hz, 1H), 8.51 (d, J=8.4 Hz, 1H), 8.34 (d, J=8.0 Hz, 1H), 8.29 (s, 1H), 8.04 (d, J=8.1 Hz, 1H), 7.98 (d, J=8.5 Hz, 1H), 7.83 (t, J=7.6 Hz, 1H), 7.69-7.61 (m, 4H), 7.38 (d, J=9.8 Hz, 1H), 4.47 (t, J=6.9 Hz, 2H), 2.54 (t, J=6.9 Hz, 2H). HRMS (ES) 368.1502 (M+H) found, 368.1509 required.

Example 10

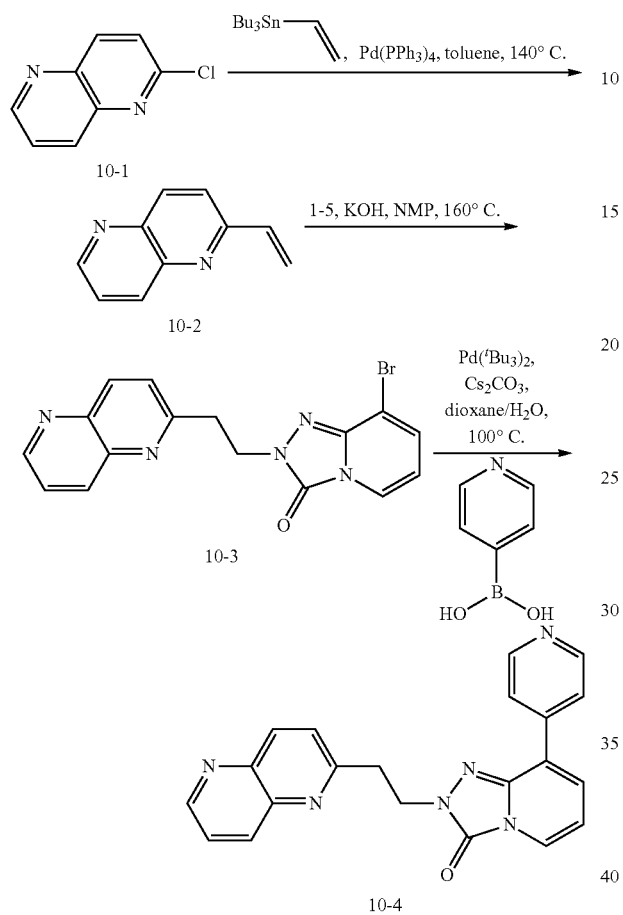

10-4

2-vinyl-1,5-naphthyridine (10-2)

2-chloro-1,5-naphthyridine (10-1) (35 g, 213 mmol) in toluene (420 mL) was treated with tributyl(vinyl)stannane (101 g, 93.4 mL, 319 mmol) and tetrakis(triphenylphosphine) palladium (36.9 g, 31.9 mmol). The mixture was heated at 140° C. under microwave irradiation for 20 min, then cooled and concentrated in vacuo. The residue was purified by silica gel flash column chromatography, eluting with 0-100% EtOAc/heptane. The fractions containing the desired product (10-2) were pooled, and after solvent removal in vacuo, 19 g (57%) of the product were obtained. LC/MS: m/z (M+H)=157.2.

2-(2-(1,5-naphthyridin-2-yl)ethyl)-8-bromo-[1,2,4] triazolo[4,3-a]pyridin-3(2H)-one (10-3)

2-Vinyl-1,5-naphthyridine (10-2) (109 mg, 0.70 mmol) and triazolopyridinone 1-5 (150 mg, 0.70 mmol) were placed in a microwave vial and dissolved in NMP (1 mL). To the mixture was added catalytic powdered KOH (7.9 mg, 0.14 mmol), and the vial was capped and heated at 160° C. under microwave irradiation for 20 min. After cooling, the mixture was diluted with CH$_2$Cl$_2$ (100 mL) and washed with water (25 mL) and brine (25 mL). The organic layer was dried over MgSO$_4$, filtered, and concentrated in vacuo. The crude material was purified by silica gel flash column chromatography (40 g cartridge), eluting with 20-100% EtOAc/hexanes, then 1-10% EtOH/EtOAc. The fractions containing the desired product (10-3) were pooled, and after solvent removal in vacuo, 160 mg (62%) of a fluffy yellow solid were obtained. LC/MS: m/z (M+H)=370.0.

2-(2-(1,5-naphthyridin-2-yl)ethyl)-8-(pyridin-4-yl)-[1,2,4]triazolo[4,3-a]pyridin-3(2H)-one (10-4)

Triazolopyridinone 10-3 (22 mg, 0.059 mmol) and pyridin-4-ylboronic acid (11 mg, 0.089 mmol) were placed in a microwave vial and dissolved in dioxane (1 mL). To the mixture was added 1 M aq. Cs$_2$CO$_3$ solution (0.12 mL, 0.12 mmol). The mixture was then sparged with N$_2$ gas for 3 min, and bis(tri-tert-butylphosphine)palladium (3.0 mg, 0.006 mmol) was added. The vial was capped and heated at 100° C. under microwave irradiation for 20 min. After cooling, the reaction mixture was diluted with EtOAc (30 mL), washed with water (10 mL) and brine (10 mL), dried over MgSO$_4$, filtered, and concentrated in vacuo. The residue was purified by silica gel flash column chromatography (12 g cartridge), eluting with 0-15% MeOH/CH$_2$Cl$_2$. The fractions containing the desired product (10-4) were pooled, and after solvent removal in vacuo, 5.0 mg (23%) of a semisolid were obtained. $^1$H NMR (300 MHz, CHCl$_3$-d): δ 8.95 (dd, J=4.2, 1.6 Hz, 1H), 8.63 (dd, J=4.8, 1.5 Hz, 2H), 8.37-8.31 (m, 2H), 7.84 (dd, J=6.9, 1.2 Hz, 1H), 7.71 (dd, J=4.8, 1.8 Hz, 2H), 7.63 (dd, J=8.7, 4.2 Hz, 1H), 7.57 (d, J=9.0 Hz, 1H), 7.39 (dd, J=6.9, 1.2 Hz, 1H), 6.64 (t, J=6.9 Hz, 1H), 4.65 (t, J=6.9 Hz, 2H), 3.60 (t, J=6.9 Hz, 2H). HRMS (ES) 369.1443 found (M+H), 369.1461 required.

Example 11

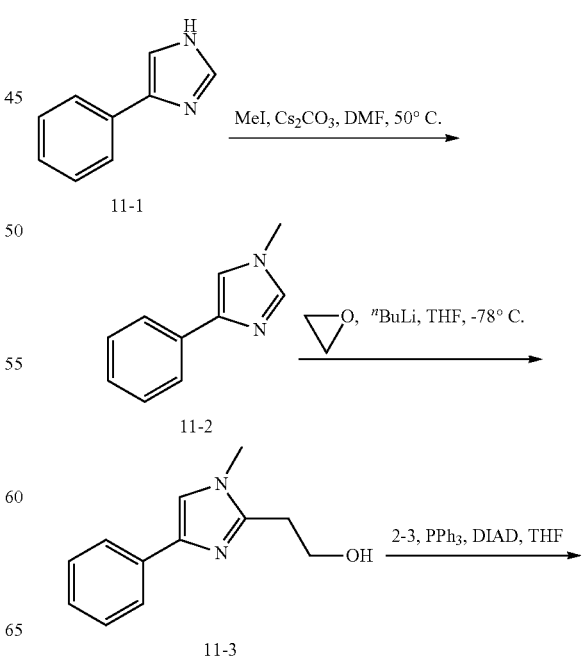

-continued

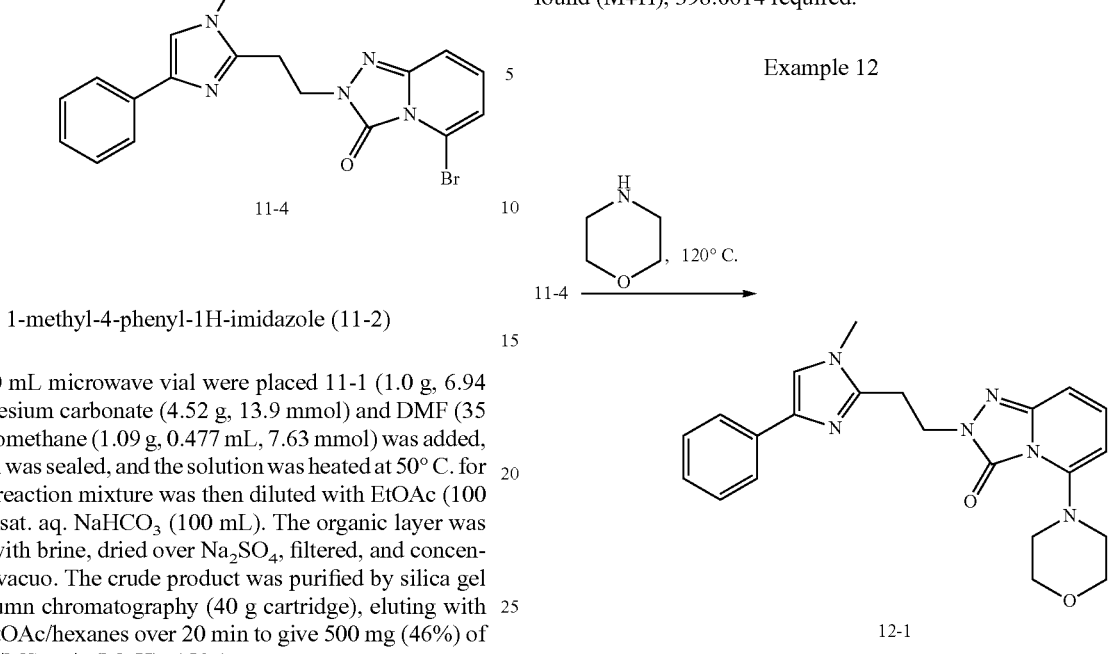

11-4

1-methyl-4-phenyl-1H-imidazole (11-2)

In a 20 mL microwave vial were placed 11-1 (1.0 g, 6.94 mmol), cesium carbonate (4.52 g, 13.9 mmol) and DMF (35 mL). Iodomethane (1.09 g, 0.477 mL, 7.63 mmol) was added, the vessel was sealed, and the solution was heated at 50° C. for 3 h. The reaction mixture was then diluted with EtOAc (100 mL) and sat. aq. NaHCO₃ (100 mL). The organic layer was washed with brine, dried over Na₂SO₄, filtered, and concentrated in vacuo. The crude product was purified by silica gel flash column chromatography (40 g cartridge), eluting with 0-70% EtOAc/hexanes over 20 min to give 500 mg (46%) of 11-2. LC/MS: m/z (M+H)=159.1.

2-(1-methyl-4-phenyl-1H-imidazol-2-yl)ethanol (11-3)

In a 25 ml flask were placed 11-2 (0.500 g, 3.16 mmol), and anhydrous THF (6 mL). The reaction was flushed with N₂ gas and cooled to −78° C. Ethylene oxide (27.3 g, 31 mL, 31.6 mmol) was added dropwise via syringe. Upon completion of addition, the reaction mixture was warmed to room temperature and stirred for 18 hours. The reaction mixture was then quenched with sat. aq. NH₄Cl (100 mL) and extracted with EtOAc (2×150 mL). The combined organic layers were washed with brine, dried over Na₂SO₄, filtered, and concentrated in vacuo. The crude product was purified by silica gel flash column chromatography (24 g cartridge), eluting with 0-100% EtOAc/hexanes to give 200 mg (31%) of 11-3. LC/MS: m/z (M+H)=203.2.

5-bromo-2-(2-(1-methyl-4-phenyl-1H-imidazol-2-yl)ethyl)-[1,2,4]triazolo[4,3-a]pyridin-3(2H)-one (11-4)

In 25 mL flask were placed 11-3 (0.200 g, 0.99 mmol), triphenylphosphine (0.26 g, 0.99 mmol), DIAD (0.200 g, 0.99 mmol) and THF (10 mL). The reaction mixture was stirred for 10 min at room temperature. 12-3 (0.254 g, 1.19 mmol) was then added and the reaction was stirred for 30 min. The mixture was concentrated in vacuo and purified by silica gel flash column chromatography (24 g cartridge), eluting with 0-100% EtOAc/hexanes to give 100 mg (25%) of 11-4. LC/MS: m/z (M+H)=398.3. ¹H NMR (500 MHz, CHCl₃-d): δ 7.70 (d, J=7.7 Hz, 2H), 7.34 (t, J=7.6 Hz, 2H), 7.21 (d, J=7.5 Hz, 1H), 7.10 (s, 1H), 7.02 (d, J=9.4 Hz, 1H), 6.82 (dd, J=9.4, 6.8 Hz, 1H), 6.57 (d, J=6.8 Hz, 1H), 4.41 (t, J=7.7 Hz, 2H), 3.67 (s, 3H), 3.25 (t, J=7.7 Hz, 2H). HRMS (ES) 398.0604 found (M+H), 398.0614 required.

Example 12

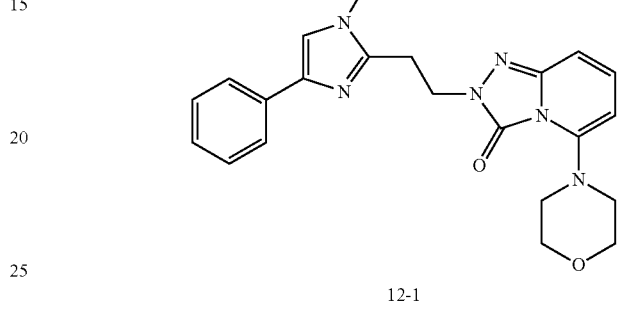

12-1

2-(2-(1-methyl-4-phenyl-1H-imidazol-2-yl)ethyl)-5-morpholino[1,2,4]thazolo[4,3-a]pyridin-3(2H)-one (12-1)

In a 2 mL microwave vial were placed 11-4 (0.025 g, 0.063 mmol) and morpholine (0.459 g, 0.461 mL, 5.27 mmol). The vial was sealed and heated in an oil bath for 15 min at 120° C. The mixture was concentrated in vacuo and purified by reverse phase HPLC (5-50% MeCN/water with 0.01% TFA additive). Fractions containing pure product were treated with sat. aq. NaHCO₃ and extracted with EtOAc. The combined extracts were washed with brine, dried over Na₂SO₄, and filtered. The filtrate was dried under reduced pressure to give 8 mg (32%) of 12-1. LC/MS: m/z (M+H)=405.5. ¹H NMR (500 MHz, CHCl₃-d): δ 7.68 (d, J=7.7 Hz, 2H), 7.31 (d, J=7.6 Hz, 2H), 7.21-7.16 (m, 1H), 7.08 (s, 1H), 6.91 (dd, J=9.3, 7.0 Hz, 1H), 6.68 (d, J=9.3 Hz, 1H), 5.60 (d, J=7.3 Hz, 1H), 4.37 (t, J=7.5 Hz, 2H), 3.90-3.86 (m, 4H), 3.74-3.70 (m, 2H), 3.64 (s, 3H), 3.21 (t, J=7.5 Hz, 2H), 2.96-2.87 (m, 2H). HRMS (ES) 405.2048 found (M+H), 405.2035 required.

Example 13

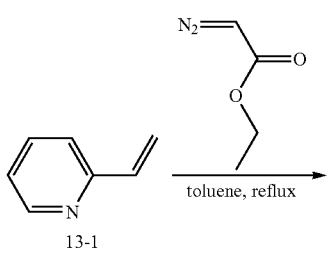

13-1

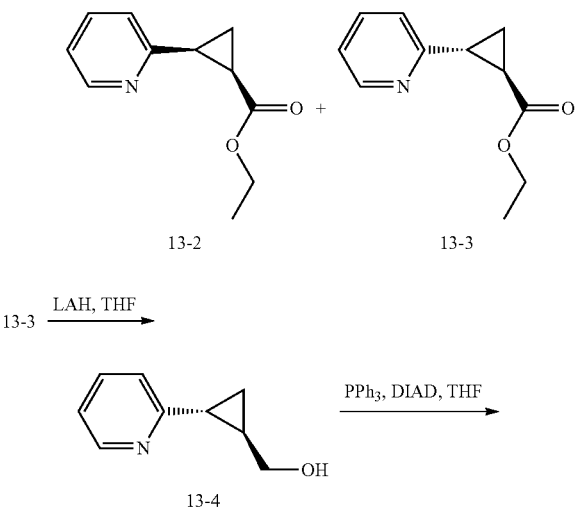

(trans-2-(pyridin-2-yl)cyclopropyl)methanol (13-4)

A solution of 13-3 (751 mg, 3.93 mmol) in THF (20 mL) was cooled to 0° C. and treated slowly with lithium aluminum hydride (3.93 mL, 3.93 mmol, 1 M solution in THF). The solution was warmed to room temperature and stirred for 20 min. The reaction mixture was then recooled to 0° C. and treated sequentially dropwise with 0.15 mL of water, 0.15 ml of 15% NaOH, and 0.45 mL of water. Sodium sulfate was added to the mixture. After stirring at room temperature for 10 min, the mixture was filtered through a pad of Celite, and the filtrate was concentrated in vacuo to afford the title compound as a pale yellow oil. The material was sufficiently pure to use in the subsequent step without further purification. LC/MS: m/z (M+H)=150.1.

5-bromo-2-(((1R,2R)-2-(pyridin-2-yl)cyclopropyl)methyl)-[1,2,4]triazolo[4,3-a]pyridin-3(2H)-one (13-5)

In 100 mL round bottom flask were placed 13-4 (697 mg, 4.67 mmol), DIAD (945 mg, 4.67 mmol), and triphenylphosphine (1.23 g, 4.67 mmol) in anhydrous THF (46.7 mL).

After stirring the yellow reaction mixture for 10 min, 2-3 (1.00 g, 4.67 mmol) was added in one portion. After 10 min, solvent was removed in vacuo, and the crude product was purified by silica gel flash column chromatography (120 g cartridge), eluting with 0-100% 1:1 EtOAc/(20:1:1 EtOH/NH$_4$OH/H$_2$O)/hexanes to give 1.21 g (75%) of 13-5. LC/MS: m/z (M+H)=345.0.

5-morpholino-2-(((1R,2R)-2-(pyridin-2-yl)cyclopropyl)methyl)-[1,2,4]triazolo[4,3-a]pyridin-3(2H)-one (13-6)

In a 1 mL microwave vial were placed 13-5 (22 mg, 0.064 mmol) and morpholine (1.00 g, 1.00 mL, 11.5 mmol). The vial was sealed and heated at 120° C. under microwave irradiation for 10 min. The reaction mixture was directly purified by reversed phase chromatography to give 14.0 mg (62%) of 13-6. $^1$H NMR δ (500 MHz, DMSO-d$_6$): δ 8.44 (d, J=5.0 Hz, 1H), 7.81 (s, 1H), 7.36 (d, J=8.0 Hz, 1H), 7.28 (s, 1H), 7.01 (dd, J=9.3, 7.0 Hz, 1H), 6.72 (d, J=9.3 Hz, 1H), 5.75 (d, J=7.0 Hz, 1H), 3.90 (dd, J=6.9, 3.9 Hz, 2H), 3.74 (t, J=4.6 Hz, 4H), 3.12-3.03 (m, 4H), 2.25 (dt, J=8.5, 4.6 Hz, 1H), 1.84 (s, 1H), 1.23-1.15 (m, 2H). HRMS (ES) 352.1761 (M+H) found, 352.1768 required.

The following compounds were prepared using the foregoing methodology, but substituting the appropriately substituted reagent, as described in the foregoing Reaction Schemes and Examples. The requisite starting materials were commercially available, described in the literature, or readily synthesized by one skilled in the art of organic synthesis without undue experimentation. Final products were purified by either gradient elution on SiO$_2$ (EtOAc/hexanes, MeOH/CH$_2$Cl$_2$, or 1:1 EtOAc/(20:1:1 EtOH/NH$_4$OH/H$_2$O)/hexanes, reverse phase flash chromatography (MeCN/H$_2$O), or preparative thin layer chromatography (EtOAc/hexanes, MeOH/CH$_2$Cl$_2$, MeOH/EtOAc or 1:1 EtOAc/(20:1:1 EtOH/NH$_4$OH/H$_2$O)/hexanes, and were isolated as free bases.

trans-ethyl 2-(pyridin-2-yl)cyclopropanecarboxylate (13-3)

A solution of 2-vinylpyridine (13-1) (2 g, 19.0 mmol) in toluene (40 ml) was treated with ethyl diazoacetate (1.97 ml, 19.0 mmol) and stirred at reflux overnight. The mixture was concentrated in vacuo, and the residue was purified by gradient elution on silica gel (0-50% EtOAc/hexanes) to elute peak 1; the solvent gradient was then ramped to 100% EtOAc to elute peak 2. This yielded the 13-3 (1.6 g, 44%) as the first eluting diastereomer, and the corresponding cis diastereomer 13-2 (914 mg, 25%) as the second eluting diastereomer, both as yellow oils. $^1$H NMR (500 MHz, CDCl$_3$): δ 8.44 (m, 1H), 7.56 (dt, J=7.6, 1.7 Hz, 1H), 7.22 (dd, J=7.8, 1.0 Hz, 1H), 7.08 (ddd, J=7.6, 4.9, 1.2 Hz, 1H), 4.17 (q, J=7.3 Hz, 2H), 2.58 (ddd, J=10.0, 6.1, 3.9 Hz, 1H), 2.25 (ddd, J=9.5, 5.6, 3.9 Hz, 1H), 1.61, (m, 2H), 1.28 (t, J=7.1 Hz, 3H). LC/MS: m/z (M+H)=192.1.

TABLE 1

| Cpd. | Structure | Name | HRMS m/z (M + H) |
|---|---|---|---|
| 1-6 | 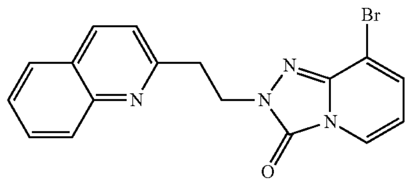 [SMILES: O=c1n(CCc2ccc3ccccc3n2)nc2c(Br)cccn12] | 8-bromo-2-(2-quinolin-2-ylethyl[1,2,4]triazolo[4,3-a]pyridin-3(2H)-one | 369.0345 found, 369.0349 required. |
| 2-4 | 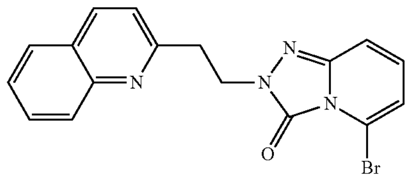 [SMILES: O=c1n(CCc2ccc3ccccc3n2)nc2cccc(Br)n12] | 5-bromo-2-(2-quinolin-2-ylethyl)[1,2,4]triazolo[4,3-a]pyridin-3(2H)-one | 369.0346 found, 369.0349 required. |
| 3-4 | 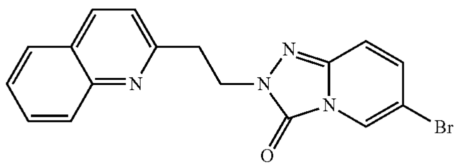 [SMILES: O=c1n(CCc2ccc3ccccc3n2)nc2ccc(Br)cn12] | 6-bromo-2-(2-quinolin-2-ylethyl)[1,2,4]triazolo[4,3-a]pyridin-3(2H)-one | 369.0348 found, 369.0349 required. |
| 4-1 | 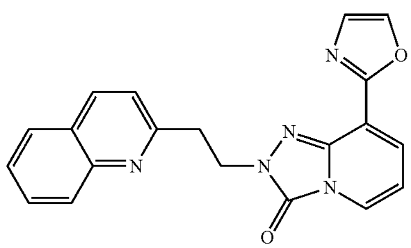 [SMILES: O=c1n(CCc2ccc3ccccc3n2)nc2c(-c3ncco3)cccn12] | 8-(1,3-oxazol-2-yl)-2-(2-quinolin-2-ylethyl)[1,2,4]triazolo[4,3-a]pyridin-3(2H)-one | 358.1299 found, 358.1302 required. |
| 5-1 | 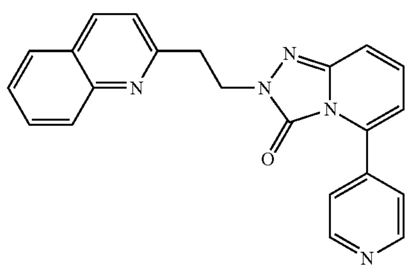 [SMILES: O=c1n(CCc2ccc3ccccc3n2)nc2cccc(-c3ccncc3)n12] | 5-pyridin-4-yl-2-(2-quinolin-2-ylethyl)[1,2,4]triazolo[4,3-a]pyridin-3(2H)-one | 368.1508 found, 368.1509 required. |
| 6-1 | 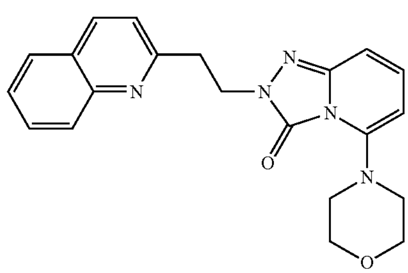 [SMILES: O=c1n(CCc2ccc3ccccc3n2)nc2cccc(N3CCOCC3)n12] | 5-morpholin-4-yl-2-(2-quinolin-2-ylethyl)[1,2,4]triazolo[4,3-a]pyridin-3(2H)-one | 376.1765 found, 376.1771 required. |
| 7-2 | 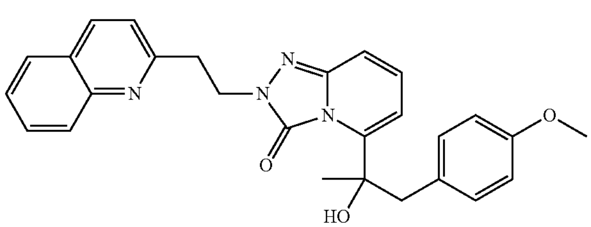 [SMILES: COc1ccc(CC(C)(O)c2cccc3nn(CCc4ccc5ccccc5n4)c(=O)n23)cc1] | 5-[1-hydroxy-1-(4-methoxyphenyl)ethyl]-2-(2-quinolin-2-ylethyl)[1,2,4]triazolo[4,3-a]pyridin-3(2H)-one | 441.1911 found, 441.1923 required. |

TABLE 1-continued

| Cpd. | Structure | Name | HRMS m/z (M + H) |
|---|---|---|---|
| 8-2 | 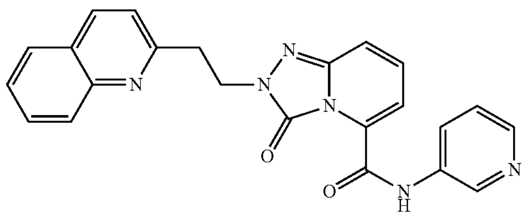 [SMILES: O=C(Nc1cccnc1)c1cccc2nn(CCc3ccc4ccccc4n3)c(=O)n12] | 3-oxo-N-pyridin-3-yl-2-(2-quinolin-2-ylethyl)-2,3-dihydro[1,2,4]triazolo[4,3-a]pyridine-5-carboxamide | 411.1546 found, 411.1567 required. |
| 9-1 | 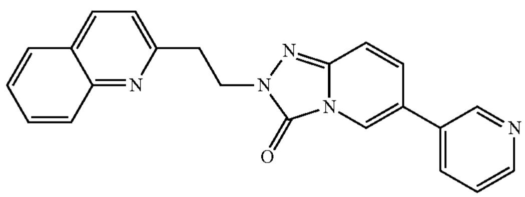 [SMILES: O=c1n(CCc2ccc3ccccc3n2)nc2ccc(-c3cccnc3)cn12] | 6-pyridin-3-yl-2-(2-quinolin-2-ylethyl)[1,2,4]triazolo[4,3-a]pyridin-3(2H)-one | 368.1502 found, 368.1509 required. |
| 10-4 | 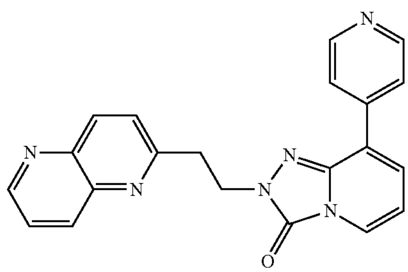 [SMILES: O=c1n(CCc2ccc3ncccc3n2)nc2c(-c3ccncc3)cccn12] | 2-[2-(1,5-naphthyridin-2-yl)ethyl]-8-pyridin-4-yl[1,2,4]triazolo[4,3-a]pyridin-3(2H)-one | 369.1443 found, 369.1461 required. |
| A-1 | 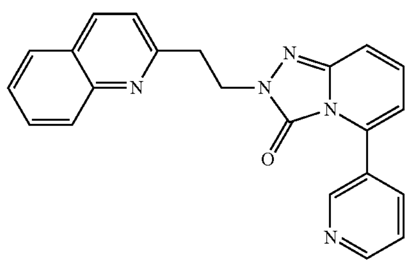 [SMILES: O=c1n(CCc2ccc3ccccc3n2)nc2cccc(-c3cccnc3)n12] | 5-pyridin-3-yl-2-(2-quinolin-2-ylethyl)[1,2,4]triazolo[4,3-a]pyridin-3(2H)-one | 368.1503 found, 368.1509 required. |
| A-2 | 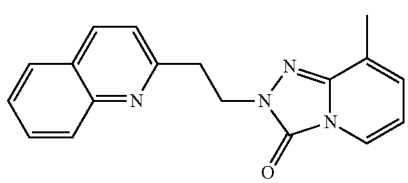 [SMILES: Cc1cccn2c(=O)n(CCc3ccc4ccccc4n3)nc12] | 8-methyl-2-(2-quinolin-2-ylethyl)[1,2,4]triazolo[4,3-a]pyridin-3(2H)-one | 305.1400 found, 305.1400 required. |
| A-3 | 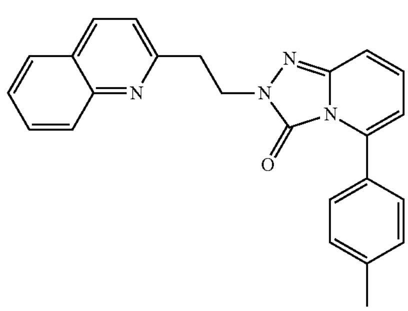 [SMILES: Cc1ccc(-c2cccc3nn(CCc4ccc5ccccc5n4)c(=O)n23)cc1] | 5-(4-methylphenyl)-2-(2-quinolin-2-ylethyl)[1,2,4]triazolo[4,3-a]pyridin-3(2H)-one | 381.1715 found, 381.1713 required. |

TABLE 1-continued

| Cpd. | Structure | Name | HRMS m/z (M + H) |
| --- | --- | --- | --- |
| A-4 | 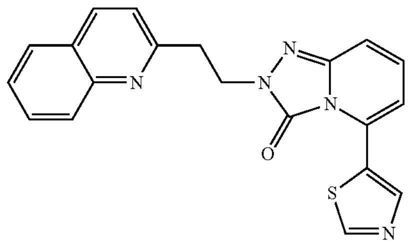 [SMILES: O=c1n(CCc2ccc3ccccc3n2)nc2cccc(-c3cncs3)n12] | 2-(2-quinolin-2-ylethyl)-5-(1,3-thiazol-5-yl)[1,2,4]triazolo[4,3-a]pyridin-3(2H)-one | 374.1068 found, 374.1073 required. |
| A-5 | 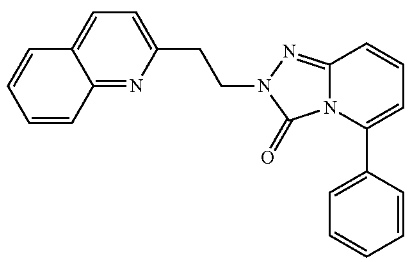 [SMILES: O=c1n(CCc2ccc3ccccc3n2)nc2cccc(-c3ccccc3)n12] | 5-phenyl-2-(2-quinolin-2-ylethyl)[1,2,4]triazolo[4,3-a]pyridin-3(2H)-one | 367.1552 found, 367.1556 required. |
| A-6 | 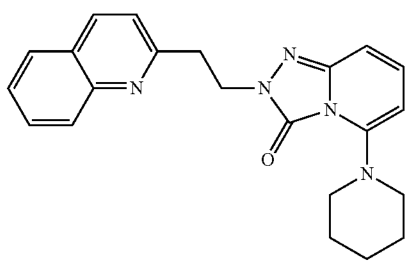 [SMILES: O=c1n(CCc2ccc3ccccc3n2)nc2cccc(N3CCCCC3)n12] | 5-piperidin-1-yl-2-(2-quinolin-2-ylethyl)[1,2,4]triazolo[4,3-a]pyridin-3(2H)-one | 374.1976 found, 374.1978 required. |
| A-7 | 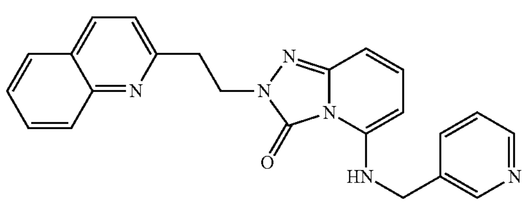 [SMILES: O=c1n(CCc2ccc3ccccc3n2)nc2cccc(NCc3cccnc3)n12] | 5-[(pyridin-3-ylmethyl)amino]-2-(2-quinolin-2-ylethyl)[1,2,4]triazolo[4,3-a]pyridin-3(2H)-one | 397.1773 found, 397.1774 required. |
| A-8 | 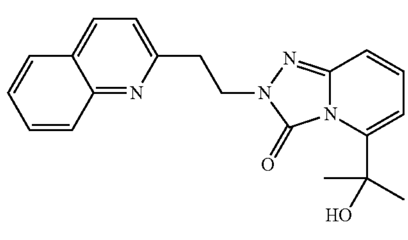 [SMILES: CC(C)(O)c1cccc2nn(CCc3ccc4ccccc4n3)c(=O)n12] | 5-(1-hydroxy-1-methylethyl)-2-(2-quinolin-2-ylethyl)[1,2,4]triazolo[4,3-a]pyridin-3(2H)-one | 349.1659 found, 349.1662 required. |
| 11-4 | 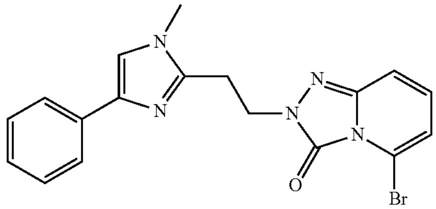 [SMILES: Cn1cc(-c2ccccc2)nc1CCn1nc2cccc(Br)n2c1=O] | 5-bromo-2-[2-(1-methyl-4-phenyl-1H-imidazol-2-yl)ethyl][1,2,4]triazolo[4,3-a]pyridin-3(2H)-one | 398.0604 found, 398.0614 required. |

TABLE 1-continued

| Cpd. | Structure | Name | HRMS m/z (M + H) |
|---|---|---|---|
| 12-1 | 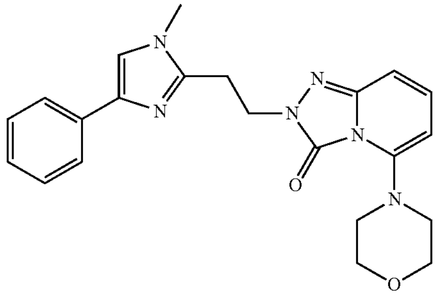 [SMILES: Cn1cc(-c2ccccc2)nc1CCn1nc2cccc(N3CCOCC3)n2c1=O] | 2-[2-(1-methyl-4-phenyl-1H-imidazol-2-yl)ethyl]-5-morpholin-4-yl[1,2,4]triazolo[4,3-a]pyridin-3(2H)-one | 405.2048 found, 405.2035 required. |
| B-1 | 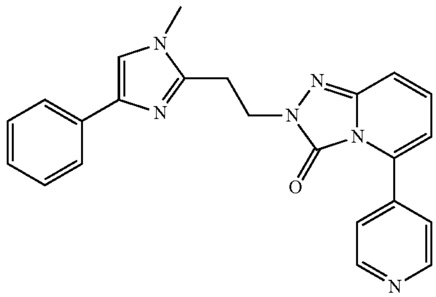 [SMILES: Cn1cc(-c2ccccc2)nc1CCn1nc2cccc(-c3ccncc3)n2c1=O] | 2-[2-(1-methyl-4-phenyl-1H-imidazol-2-yl)ethyl]-5-pyridin-4-yl[1,2,4]triazolo[4,3-a]pyridin-3(2H)-one | 397.1765 found, 397.1774 required. |
| 13-6 | 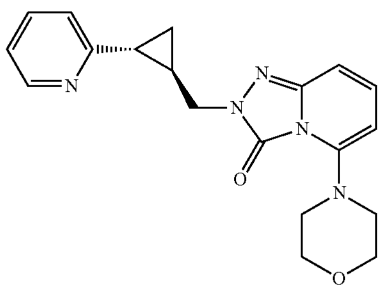 [SMILES: O=c1n(C[C@@H]2C[C@H]2c2ccccn2)nc2cccc(N3CCOCC3)n12] | 5-morpholino-2-(((1R,2R)-2-(pyridin-2-yl)cyclopropyl)methyl)-[1,2,4]triazolo[4,3-a]pyridin-3(2H)-one | 352.1761 found, 352.1768 required. |

The compounds of the following examples had activity in inhibiting the human PDE10 enzyme in the aforementioned assays with a $K_i$ of about 0.1 nM to about 100 nM: 1-6, 2-4, 4-1, 5-1, 6-1, 7-2, 8-2, A-1, A-2, A-3, A-4, A-5, A-6, A-7, A-8, 11-4, 12-1, B-1.

The compounds of the following examples had activity in inhibiting the human PDE10 enzyme in the aforementioned assays with a $K_i$ of about 0.1 nM to about 10 nM: 5-1, 6-1, A-1, 11-4, 12-1, B-1.

The following table shows representative data for the compounds of the Examples as PDE10 inhibitors as determined by the foregoing assays wherein the PDE10 $K_i$ is a measure of the ability of the test compound to inhibit the action of the PDE10 enzyme. Representative compounds of the invention had the $K_i$ values specified below in the above-described assay.

TABLE 2

| Compound | PDE10A $K_i$ (nM) |
|---|---|
| 1-6 | 37 |
| 2-4 | 59 |
| 3-4 | 155 |
| 4-1 | 22 |
| 5-1 | 4.4 |
| 6-1 | 2.5 |
| 7-2 | 11 |

TABLE 2-continued

| Compound | PDE10A $K_i$ (nM) |
|---|---|
| 8-2 | 97 |
| 9-1 | 510 |
| 10-4 | 103 |
| A-1 | 9.0 |
| A-2 | 74 |
| A-3 | 17 |
| A-4 | 23 |
| A-5 | 20 |
| A-6 | 19 |
| A-7 | 12 |
| A-8 | 72 |
| 11-4 | 7.2 |
| 12-1 | 0.41 |
| B-1 | 2.0 |
| 13-6 | 546 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

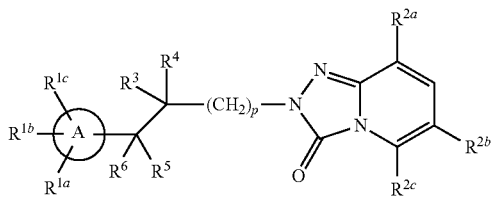

wherein:
A is heterocyclyl selected from the group consisting of
(1) imidazolyl, and
(2) quinolinyl;
$R^{1a}$, $R^{1b}$ and $R^{1c}$ may be absent if the valency of A does not permit such substitution and are independently selected from the group consisting of:
(1) hydrogen,
(2) halogen,
(3) hydroxyl,
(4) —(C=O)$_m$—O$_n$—C$_{1-6}$ alkyl, where m is 0 or 1, n is 0 or 1 (wherein if m is 0 or n is 0, a bond is present) and where the alkyl is unsubstituted or substituted with one or more substituents selected from $R^{13}$,
(5) —(C=O)$_m$—O$_n$—C$_{3-6}$cycloalkyl, where the cycloalkyl is unsubstituted or substituted with one or more substituents selected from $R^{13}$,
(6) —(C=O)$_m$—C$_{2-4}$ alkenyl, where the alkenyl is unsubstituted or substituted with one or more substituents selected from $R^{13}$,
(7) —(C=O)$_m$—C$_{2-4}$ alkynyl, where the alkynyl is unsubstituted or substituted with one or more substituents selected from $R^{13}$,
(8) —(C=O)$_m$—O$_n$-phenyl or —(C=O)$_m$—O$_n$-naphthyl, where the phenyl or naphthyl is unsubstituted or substituted with one or more substituents selected from $R^{13}$,
(9) —(C=O)$_m$—O$_n$-heteroaryl, where the heteroaryl is unsubstituted or substituted with one or more substituents selected from $R^{13}$,
(10) —(C=O)$_m$—NR$^{10}$R$^{11}$, wherein $R^{10}$ and $R^{11}$ are independently selected from the group consisting of:
 (a) hydrogen,
 (b) C$_{1-6}$ alkyl, which is unsubstituted or substituted with $R^{14}$,
 (c) C$_{3-6}$ alkenyl, which is unsubstituted or substituted with $R^{14}$,
 (d) C$_{3-6}$ alkynyl, which is unsubstituted or substituted with $R^{14}$,
 (e) C$_{3-6}$ cycloalkyl which is unsubstituted or substituted with $R^{14}$,
 (f) phenyl, which is unsubstituted or substituted with $R^{14}$, and
 (g) heteroaryl, which is unsubstituted or substituted with $R^{14}$,
(11) —S(O)$_2$—NR$^{10}$R$^{11}$,
(12) —S(O)$_q$—R$^{12}$, where q is 0, 1 or 2 and where $R^{12}$ is selected from the definitions of $R^{10}$ and $R^{11}$,
(13) —CO$_2$H,
(14) —CN, and
(15) —NO$_2$;

$R^{2b}$ is hydrogen
$R^{2a}$, and $R^{2c}$, are independently selected from the group consisting of:
(1) hydrogen,
(2) halogen,
(3) hydroxyl,
(4) —(C=O)$_m$—O$_n$—C$_{1-6}$ alkyl, where the alkyl is unsubstituted or substituted with one or more substituents of $R^{13}$,
(5) —(C=O)$_m$—O$_n$—C$_{3-6}$cycloalkyl, where the cycloalkyl is unsubstituted or substituted with one or more substituents selected from $R^{13}$,
(6) —(C=O)$_m$—C$_{2-4}$ alkenyl, where the alkenyl is unsubstituted or substituted with one or more substituents selected from $R^{13}$,
(7) —(C=O)$_m$—C$_{2-4}$ alkynyl, where the alkynyl is unsubstituted or substituted with one or more substituents selected from $R^{13}$,
(9) —(C=O)$_m$—O$_n$-heterocyclyl, where the heterocyclyl is unsubstituted or substituted with one or more substituents selected from $R^{13}$,
(10) —(C=O)$_m$—NR$^{10}$R$^{11}$,
(11) —S(O)$_2$—NR$^{10}$R$^{11}$,
(12) —S(O)$_q$—R$^{12}$,
(13) —CO$_2$H,
(14) —CN, and
(15) —NO$_2$;

$R^3$, $R^4$, $R^5$ and $R^6$ are independently selected from the group consisting of:
(1) hydrogen,
(2) halogen, and
(3) —C$_{1-6}$ alkyl,
or $R^3$ and $R^5$ are joined together to form a cyclopropyl ring;

$R^{13}$ is selected from the group consisting of:
(1) halogen,
(2) hydroxyl,
(3) —(C=O)$_m$—O$_n$—C$_{1-6}$ alkyl, where the alkyl is unsubstituted or substituted with one or more substituents selected from $R^{14}$,
(4) —O$_n$—(C$_{1-3}$)perfluoroalkyl,
(5) —(C=O)$_m$—O$_n$—C$_{3-6}$cycloalkyl, where the cycloalkyl is unsubstituted or substituted with one or more substituents selected from $R^{14}$,
(6) —(C=O)$_m$—C$_{2-4}$ alkenyl, where the alkenyl is unsubstituted or substituted with one or more substituents selected from $R^{14}$,
(7) —(C=O)$_m$—C$_{2-4}$ alkynyl, where the alkynyl is unsubstituted or substituted with one or more substituents selected from $R^{14}$,
(8) —(C=O)$_m$—O$_n$-phenyl or —(C=O)$_m$—O$_n$-naphthyl, where the phenyl or naphthyl is unsubstituted or substituted with one or more substituents selected from $R^{14}$,
(9) —(C=O)$_m$—O$_n$-heteroaryl, where the heteroaryl is unsubstituted or substituted with one or more substituents selected from $R^{14}$,
(10) —(C=O)$_m$—NR$^{10}$R$^{11}$,
(11) —S(O)$_2$—NR$^{10}$R$^{11}$,
(12) —S(O)$_q$—R$^{12}$,
(13) —CO$_2$H,
(14) —CN, and
(15) —NO$_2$;

$R^{14}$ is selected from the group consisting of:
(1) hydroxyl,
(2) halogen,
(3) C$_{1-6}$ alkyl, (4) —$C_{3-6}$cycloalkyl,
(5) —O—$C_{1-6}$alkyl,
(6) —O(C=O)—$C_{1-6}$ alkyl,
(7) —NH—$C_{1-6}$alkyl,
(8) phenyl,
(9) heteroaryl,
(10) —$CO_2$H, and
(11) —CN;

p is 0 or 1, wherein when p is 0 a bond is present;
or a pharmaceutically acceptable salt thereof.

2. The compound of claim 1 of the formula Ia:

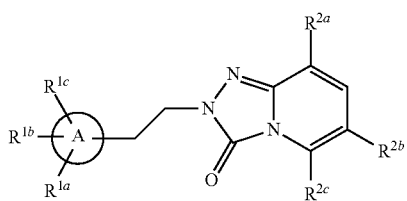

Ia or a pharmaceutically acceptable salt thereof.

3. The compound of claim 1 wherein A is quinolinyl.
4. The compound of claim 1 wherein A is imidazolyl.
5. The compound of claim 1 wherein $R^{2b}$ is hydrogen, and $R^{2a}$ and $R^{2c}$ are independently selected from the group consisting of:
   (1) hydrogen,
   (2) chloro,
   (3) fluoro,
   (4) bromo,
   (5) methyl,
   (6) isopropoxy,
   (7) methoxy,
   (8) t-butoxy,
   (9) imidazolyl,
   (10) isothiazolyl,
   (11) oxazolyl,
   (12) morpholinyl,
   (13) pyrazolyl,
   (14) pyridyl,
   (15) tetrazolyl, and
   (16) thiazolyl.

6. The compound of claim 1 wherein $R^3$ is hydrogen, $R^4$ is hydrogen, $R^5$ is hydrogen, and $R^6$ is hydrogen.

7. A compound which is selected from the group consisting of:
   8-bromo-2-(2-(quinolin-2-yl)ethyl)-[1,2,4]triazolo[4,3-a]pyridin-3(2H)-one;
   5-bromo-2-(2-(quinolin-2-yl)ethyl)-[1,2,4]triazolo[4,3-a]pyridin-3(2H)-one;
   6-bromo-2-(2-(quinolin-2-yl)ethyl)-[1,2,4]triazolo[4,3-a]pyridin-3(2H)-one;
   8-(oxazol-2-yl)-2-(2-(quinolin-2-yl)ethyl)-[1,2,4]triazolo[4,3-a]pyridin-3(2H)-one;
   5-(pyridin-4-yl)-2-(2-(quinolin-2-yl)ethyl)-[1,2,4]triazolo[4,3-a]pyridin-3(2H)-one;
   5-morpholino-2-(2-(quinolin-2-yl)ethyl)-[1,2,4]triazolo[4,3-a]pyridin-3(2H)-one;
   5-(2-hydroxy-1-(4-methoxyphenyl)propan-2-yl)-2-(2-(quinolin-2-yl)ethyl)-[1,2,4]triazolo[4,3-a]pyridin-3(2H)-one;
   3-oxo-N-(pyridin-3-yl)-2-(2-(quinolin-2-yl)ethyl)-2,3-dihydro-[1,2,4]triazolo[4,3-a]pyridine-5-carboxamide;
   5-bromo-2-(2-(1-methyl-4-phenyl-1H-imidazol-2-yl)ethyl)-[1,2,4]triazolo[4,3-a]pyridin-3(2H)-one;
   2-(2-(1-methyl-4-phenyl-1H-imidazol-2-yl)ethyl)-5-morpholino-[1,2,4]triazolo[4,3-a]pyridin-3(2H)-one;
   5
   8-bromo-2-(2-quinolin-2-ylethyl)[1,2,4]triazolo[4,3-a]pyridin-3(2H)-one;
   5-bromo-2-(2-quinolin-2-ylethyl)[1,2,4]triazolo[4,3-a]pyridin-3(2H)-one;
   6-bromo-2-(2-quinolin-2-ylethyl)[1,2,4]triazolo[4,3-a]pyridin-3(2H)-one;
   8-(1,3-oxazol-2-yl)-2-(2-quinolin-2-ylethyl)[1,2,4]triazolo[4,3-a]pyridin-3(2H)-one;
   5-pyridin-4-yl-2-(2-quinolin-2-ylethyl)[1,2,4]triazolo[4,3-a]pyridin-3(2H)-one;
   5-morpholin-4-yl-2-(2-quinolin-2-ylethyl)[1,2,4]triazolo[4,3-a]pyridin-3(2H)-one;
   5-[1-hydroxy-1-(4-methoxyphenyl)ethyl]-2-(2-quinolin-2-ylethyl)[1,2,4]triazolo[4,3-a]pyridin-3(2H)-one;
   3-oxo-N-pyridin-3-yl-2-(2-quinolin-2-ylethyl)-2,3-dihydro[1,2,4]triazolo[4,3-a]pyridine-5-carboxamide;
   6-pyridin-3-yl-2-(2-quinolin-2-ylethyl)[1,2,4]triazolo[4,3-a]pyridin-3(2H)-one;
   5-pyridin-3-yl-2-(2-quinolin-2-ylethyl)[1,2,4]triazolo[4,3-a]pyridin-3(2H)-one;
   8-methyl-2-(2-quinolin-2-ylethyl)[1,2,4]triazolo[4,3-a]pyridin-3(2H)-one;
   5-(4-methylphenyl)-2-(2-quinolin-2-ylethyl)[1,2,4]triazolo[4,3-a]pyridin-3(2H)-one;
   2-(2-quinolin-2-ylethyl)-5-(1,3-thiazol-5-yl)[1,2,4]triazolo[4,3-a]pyridin-3(2H)-one;
   5-phenyl-2-(2-quinolin-2-ylethyl)[1,2,4]triazolo[4,3-a]pyridin-3(2H)-one;
   5-piperidin-1-yl-2-(2-quinolin-2-ylethyl)[1,2,4]triazolo[4,3-a]pyridin-3(2H)-one;
   5-[(pyridin-3-ylmethyl)amino]-2-(2-qyinolin-2-ylethyl)[1,2,4]triazolo[4,3-a]pyridin-3(2H)-one;
   5-(1-hydroxy-1-methylethyl)-2-(2-quinolin-2-ylethyl)[1,2,4]triazolo[4,3-a]pyridin-3(2H)-one;
   5-bromo-2-[2-(1-methyl-4-phenyl-1H-imidazol-2-yl)ethyl][1,2,4]triazolo[4,3-a]pyridin-3(2H)-one;
   2-[2-(1-methyl-4-phenyl-1H-imidazol-2-yl)ethyl]-5-morpholin-4-yl[1,2,4]triazolo[4,3-a]pyridin-3(2H)-one;
   2-[2-(1-methyl-4-phenyl-1H-imidazol-2-yl)ethyl]-5-pyridin-4-yl[1,2,4]triazolo[4,3-a]pyridin-3(2H)-one; and
   or a pharmaceutically acceptable salt thereof.

8. A pharmaceutical composition which comprises a pharmaceutically acceptable carrier and a compound of claim 1 or a pharmaceutically acceptable salt thereof.

9. A compound of claim 1 or a pharmaceutically acceptable salt thereof for use in medicine.

* * * * *